US007589080B2

(12) United States Patent  
Hildreth

(10) Patent No.: US 7,589,080 B2  
(45) Date of Patent: Sep. 15, 2009

(54) β-CYCLODEXTRIN COMPOSITIONS, AND USE TO PREVENT TRANSMISSION OF SEXUALLY TRANSMITTED DISEASES

(75) Inventor: James E. Hildreth, Baltimore, MD (US)

(73) Assignee: The Johns Hopkins University School of Medicine, Baltimore, MD (US)

( * ) Notice: Subject to any disclaimer, the term of this patent is extended or adjusted under 35 U.S.C. 154(b) by 310 days.

(21) Appl. No.: 11/605,037

(22) Filed: Nov. 27, 2006

(65) Prior Publication Data

US 2007/0088000 A1    Apr. 19, 2007

Related U.S. Application Data

(63) Continuation of application No. 11/025,661, filed on Dec. 28, 2004, now Pat. No. 7,202,231, which is a continuation of application No. 09/802,779, filed on Mar. 8, 2001, now Pat. No. 6,835,717, which is a continuation-in-part of application No. 09/801,393, filed on Mar. 7, 2001, now abandoned.

(60) Provisional application No. 60/267,199, filed on Feb. 7, 2001, provisional application No. 60/187,784, filed on Mar. 8, 2000.

(51) Int. Cl.  
*A01N 43/04* (2006.01)  
*A61K 31/715* (2006.01)

(52) U.S. Cl. .................. 514/58; 514/54; 514/841; 514/931; 514/934

(58) Field of Classification Search .......... None  
See application file for complete search history.

(56) References Cited

U.S. PATENT DOCUMENTS

| | | | |
|---|---|---|---|
| 5,100,878 A | 3/1992 | Geber | 514/58 |
| 5,725,875 A | 3/1998 | Noll et al. | 424/445 |
| 5,814,330 A | 9/1998 | Putteman et al. | 424/434 |
| 5,819,742 A | 10/1998 | Sokal et al. | 128/830 |
| 5,897,856 A | 4/1999 | Trinh et al. | 424/65 |
| 5,985,313 A | 11/1999 | Neurath et al. | 424/434 |
| 6,068,851 A | 5/2000 | Bergeron et al. | 424/424 |
| 6,159,491 A | 12/2000 | Durrani | 424/430 |
| 6,165,493 A | 12/2000 | Neurath et al. | 424/434 |
| 6,284,231 B1 | 9/2001 | Trinh et al. | 424/76.1 |
| 6,294,186 B1 | 9/2001 | Beerse et al. | 424/405 |
| 6,500,460 B1 | 12/2002 | Bergeron et al. | 424/486 |
| 2002/0128227 A1 | 9/2002 | Hildreth | 514/58 |
| 2003/0220294 A1 | 11/2003 | Wallace et al. | 514/58 |
| 2004/0043041 A1 | 3/2004 | Baker, Jr. et al. | 424/400 |
| 2005/0148570 A1 | 7/2005 | Huang et al. | 514/192 |

FOREIGN PATENT DOCUMENTS

| | | |
|---|---|---|
| DE | 198 14 815 A1 | 10/1999 |
| EP | 0 531 016 A2 | 3/1993 |
| EP | 0 423 240 B1 | 11/1995 |
| WO | WO 90/00596 | 1/1990 |
| WO | WO 95/31178 | 11/1995 |
| WO | WO 97/18839 | 5/1997 |
| WO | WO 98/55148 | 12/1998 |
| WO | WO 99/62958 | 12/1999 |
| WO | WO 99/65497 | 12/1999 |
| WO | WO 03/080080 | 10/2003 |

OTHER PUBLICATIONS

Han et al., *Yakhak Hoechi*, 38(4):440-450, Abstract (1994).  
Irie and Uekama, "Cyclodextrins in Peptide and Protein Delivery," *Advanced Drug Delivery Reviews*, 36:101-123, Elsevier (1999).  
Matsuda and Arima, "Cyclodextrins in Transdermal and Rectal Delivery," *Advanced Drug Delivery Reviews*, 36:81-99, Elsevier (1999).  
Rendleman, Jr., "Enhancement of Cyclodextrin Production through Use of Debranching Enzymes," USDA Agricultural Research Service, http://www.nal.usda.gov/ttic/tektran/data/000007/33/0000073334.html, (Dec. 18, 1998).  
Witvrouw and De Clercq, "Sulfated Polysaccharides Extracted from Sea Algae as Potential Antiviral Drugs," *Gen. Pharmac.*, 29(4):497-511, Elsevier Science Inc. (1997).  
Castro-Hermida et al., "Treatment with β-cyclodextrin of natural *Cryptosporidium parvum* infections in lambs under field conditions", *International Journal for Parasitology*, 31:1134-1137 (2001).  
Khanna et al., "Vaginal transmission of cell-associated HIV-1 in the mouse is blocked by a topical, membrane-modifying agent", *The Journal of Clinical Investigation*, 109(2):205-211 (2002).  
Liao et al., "Lipid Rafts and HIV Pathogenesis: Host Membrane Cholesterol Is Required for Infection by HIV Type 1", *Aids Research And Human Retroviruses*, 17(11):1009-1019 (2001).  
Moriya et al., "Potent Inhibitory Effect of a Series of Modified Cyclodextrin Sulfates (Mcds) on the Replication of HIV-1 in Vitro", *Journal of Medicinal Chemistry*, 34(7):2301-2304 (1991).  
Pitha & Anand, "Alpha-cyclodextrin sulphate, an anti-HIV agent, retains its antiviral effect in the presence of hydrocortisol phosphate", *Antiviral Chemistry & Chemotherapy*, 4(1):65-66 (1993).  
U.S. Appl. No. 60/366429, filed Mar. 21, 2002.

*Primary Examiner*—Patrick T Lewis  
(74) *Attorney, Agent, or Firm*—DLA Piper LLP (US)

(57) ABSTRACT

Methods of reducing the risk of transmission of a sexually transmitted pathogen by contacting the pathogen or cells susceptible to infection by the pathogen with a β-cyclodextrin are provided. Methods for reducing the risk of transmission of a sexually transmitted pathogen to or from a subject by contacting the pathogen or cells susceptible to the pathogen in the subject with a pharmaceutical composition containing a β-cyclodextrin also are provided. Accordingly, pharmaceutical compositions, which include 1) a β-cyclodextrin, which is in an amount that blocks passage of the pathogen through lipid rafts in the membrane of a cell susceptible to the pathogen, and 2) a contraceptive, an agent for treating a sexually transmitted disease, a lubricant, or a combination thereof, are provided, as are composition formulated from a solid substrate that contains an amount of β-cyclodextrin useful for reducing the risk of transmission of a sexually transmitted pathogen.

19 Claims, No Drawings

β-CYCLODEXTRIN COMPOSITIONS, AND USE TO PREVENT TRANSMISSION OF SEXUALLY TRANSMITTED DISEASES

CROSS REFERENCE TO RELATED APPLICATIONS

This application is a continuation application of U.S. application Ser. No. 11/025,661 filed Dec. 28, 2004, now U.S. Pat. No. 7,202,231; which is a continuation application of U.S. application Ser. No. 09/802,779 filed Mar. 8, 2001, now issued as U.S. Pat. No. 6,835,717; which is a continuation-in-part application of U.S. application Ser. No. 09/801,393 filed Mar. 7, 2001, now abandoned; which claims the benefit under 35 USC § 119(e) to U.S. application Ser. No. 60/267, 199 filed Feb. 7, 2001, now abandoned and to U.S. Application Ser. No. 60/187,784 filed Mar. 8, 2000, now abandoned. The disclosure of each of the prior applications is considered part of and is incorporated by reference in the disclosure of this application.

GRANT INFORMATION

This invention was made in part with government support under Grant Nos. AI31806 and AI4629 awarded by the National Institutes of Health and Grant No. HD39613 awarded by the U.S. Public Health Service. The government has certain rights in this invention.

BACKGROUND OF THE INVENTION

1. Field of the Invention

The invention relates generally to agents and methods for preventing a viral or microbial infection and, more specifically, to compositions containing a β-cyclodextrin and methods of using such compositions to reduce the risk of transmission of a sexually transmitted disease.

2. Background Information

Sexually transmitted diseases (STDs) are among the most common types of infections. Three bacterial STDs—gonorrhea, chlamydial infections, and syphilis—are particularly common, and account for a great deal of morbidity, including infertility, ectopic pregnancy, and loss of productivity (see Harrison's "Principles of Internal Among the viral STDs, human papilloma virus and hepatitis B virus are among the most common, and are associated with cervical carcinoma and hepatocellular carcinoma, respectively.

In the past couple of decades, acquired immunodeficiency disease (AIDS) associated with sexual transmission of human immunodeficiency virus (HIV) has emerged as a global health threat. In industrialized countries, education as to the use of condoms and the practice of "safe sex" reduced the levels of new HIV infection and of AIDS deaths following a peak in the mid-1990's. However, the decreased number of AIDS deaths and the availability of medications that appear to increase the life spans of AIDS patients may have created a false sense of security, and it now appears that this trend may reverse. In many non-industrialized countries, AIDS is an epidemic, and it is not inconceivable that millions may die from this disease in the next few years.

HIV can be transmitted in a number of ways, including through contaminated blood products, and from mother to offspring during gestation, child birth or breast feeding. However, newly acquired HIV infections are largely the result of sexual contact, particularly heterosexual contact. A number of factors appear to determine whether HIV is transmitted sexually, including the type of sex act, susceptibility of the exposed partner, infectivity of the infected partner, and the biological properties of the particular HIV subtype.

Prevention of the spread of HIV infection requires interventions of both the infected and uninfected populations. In particular, since only a small percentage of HIV-infected individuals are aware of their carrier status, a significant prevention effort must be made by the susceptible population. Mechanical barriers such as condoms can be effective in preventing sexual transmission of HIV. However, this method is not always accepted by male partners, and can be impractical for use by women. Topical microbicides currently available have proven inadequate, and the widely used surfactant microbicide, nonoxynol-9, which is used as a spermicide, may actually increase HIV infection by inducing genital ulcerations. Thus, in the absence of an effective vaccine, other biomedical methods must be identified, particularly those that can be practiced by the susceptible population.

Semen from HIV infected men and cervical mucus from HIV infected women contain free virus as well as HIV-infected cells and, sexual transmission of HIV may occur due to both forms of the virus. Thus, a need exists for a therapeutic agent that reduces or eliminates transmission of free HIV as well as cell-associate virus infection, thereby reducing the risk of transmission of HIV and other sexually transmitted pathogens. The present invention satisfies this need and provides additional advantages.

SUMMARY OF THE INVENTION

The present invention relates to methods of reducing the risk of transmission of a sexually transmitted pathogen, including cell-associated and cell-free sexually transmitted pathogens. In one embodiment, a method of the invention is performed by contacting the pathogen or cells susceptible to infection by the pathogen with a β-cyclodextrin (βCD). The pathogen can be any pathogen involved in the etiology of a sexually transmitted disease, particularly a pathogen that infects a susceptible cell through contact with lipid rafts in the membrane of the cell. As such, the pathogen can be an enveloped virus, for example, an immunodeficiency virus such as human immunodeficiency virus (HIV), a T lymphotrophic virus such as human T lymphotrophic virus (HTLV), a herpesvirus such as a herpes simplex virus (HSV), a measles virus, or an influenza virus. The pathogen also can be a microbial pathogen, for example, a bacterium, a yeast such as a *Candida* spp., a mycoplasma, a protozoan such as a *Trichomona* spp., or a *Chlamydia* spp. The βCD can be any βCD derivative, for example, 2-hydroxypropyl-β-cyclodextrin.

In another embodiment, a method of the invention provides a means to reduce the risk of transmission of a sexually transmitted pathogen to or from a subject, which can be any subject susceptible to a sexually transmitted disease, for example, a vertebrate, particularly a mammal, including a human. Such a method can be performed, for example, by contacting the pathogen or cells susceptible to infection by the pathogen in the subject with a pharmaceutical composition comprising a β-cyclodextrin (βCD), thereby reducing the risk of the subject becoming infected with the sexually transmitted the pathogen. Such a method also can be performed, for example, by contacting the pathogen or cells susceptible to infection by the pathogen in a subject having a sexually transmitted disease with a pharmaceutical composition comprising a βCD, thereby reducing the risk of transmission of the sexually transmitted disease by the subject.

he cells susceptible to infection by the pathogen can be any cells depending, in part, on the pathogen, including epithelial cells, particularly vaginal epithelial cells or rectal epithelial cells. Furthermore, the cells susceptible to infection, as well as the pathogen in a cell-free form, can be present in a secretion produced by the subject, for example, in semen or in a vaginal secretion. The pharmaceutical composition can be formulated in a solution, a gel, a foam, an ointment, a cream, a paste, a spray, or the like; or can be formulated as a component of a suppository, a film, a sponge, a condom, a bioadhesive polymer, a diaphragm, or the like; and can contain, in addition to the βCD, one or more agents useful to a sexually active subject, for example, a contraceptive, an antimicrobial or antiviral agent, a lubricant, or a combination thereof.

The present invention also relates to a pharmaceutical composition, which includes 1) βCD, which is in an amount that blocks passage of the pathogen through lipid rafts in the membrane of a cell susceptible to the pathogen, and 2) a contraceptive, an antimicrobial or antiviral agent, a lubricant, or a combination thereof. A contraceptive useful in a pharmaceutical composition of the invention can be any contraceptive, for example, a spermicide. Similarly, an antimicrobial or antiviral agent for treating a sexually transmitted disease can be any agent that generally is used to treat or prevent infection by a sexually transmitted pathogen, or an opportunistic pathogen associated with a sexually transmitted disease, including, for example, an antibiotic.

The present invention further relates to a composition, comprising a solid substrate that contains an amount of βCD useful for reducing the risk of transmission of a sexually transmitted pathogen. The solid substrate can be a barrier, which is composed of a relatively impermeable substrate, for example, a condom, diaphragm, vaginal film or glove, which contains the βCD at least on its surface; or can be composed of an absorptive material, for example, a sponge or a tampon, which contains the β-cyclodextrin incorporated therein.

DETAILED DESCRIPTION OF THE INVENTION

The present invention provides methods of reducing the risk of transmission of a sexually transmitted pathogen. A method of the invention is based, in part, on the determination that entry of a sexually transmitted pathogen, for example, a sexually transmitted enveloped virus, into a cell depends, at least in part, on the presence of lipid rafts in the membranes of cells susceptible to the pathogen, and the determination that contact of such susceptible cells or of the pathogen with a β-cyclodextrin, which disrupts the structure of lipid rafts, blocks the ability of the pathogen to infect an otherwise susceptible cell.

β-cyclodextrins (βCDs) are widely used as solubilizing agents, stabilizers, and inert excipients in pharmaceutical compositions (see U.S. Pat. Nos. 6,194,430; 6,194,395; and 6,191,137, each of which is incorporated herein by reference). βCDs are cyclic compounds containing seven units of I-(1→4) linked D-glucopyranose units, and act as complexing agents that can form inclusion complexes and have concomitant solubilizing properties (see U.S. Pat. No. 6,194,395; see, also, Szejtli, J. Cyclodextrin Technol. 1988). As disclosed herein, βCDs also can block passage of a sexually transmitted pathogen through the membrane of a susceptible cell by disrupting the lipid rafts in cell membrane.

The compositions and methods of the invention are exemplified using 2-hydroxypropyl-βCD (2-OH-βCD). However, any βCD derivative can be used in a composition or method of the invention, provided the βCD derivative disrupts lipid rafts in the membranes of cells susceptible to a sexually transmitted pathogen without causing undesirable side effects (see Example 3). βCDs act, in part, by removing cholesterol from cell membranes, and different βCDs are variably effective in such removal. For example, methyl-βCD removes cholesterol from cell membranes very efficiently and quickly and, as a result, can be toxic to cells, which require cholesterol for membrane integrity and viability. In comparison, a βCD derivative such as 2-OH-βCD can effectively remove cholesterol from cells without producing undue toxicity. Thus, it will be recognized that a βCD useful in a composition or method of the invention is one that removes cholesterol in an amount that disrupts lipid rafts, without substantially reducing cell viability (see, for example, Rothblat and Phillips, J. Biol. Chem. 257:4775-4782, 1982, which is incorporated herein by reference).

βCDs useful in the present invention include, for example, βCD derivatives wherein one or more of the hydroxy groups is substituted by an alkyl, hydroxyalkyl, carboxyalkyl, alkylcarbonyl, carboxyalkoxyalkyl, alkylcarbonyloxyalkyl, alkoxycarbonylalkyl or hydroxy-(mono or polyalkoxy)alkyl group or the like; and wherein each alkyl or alkylene moiety contains up to about six carbons. Substituted βCDs that can be used in the present invention include, for example, polyethers (see, for example, U.S. Pat. No. 3,459,731, which is incorporated herein by reference); ethers, wherein the hydrogen of one or more βCD hydroxy groups is replaced by C1 to C6 alkyl, hydroxy-C1-C6-alkyl, carboxy-C1-C6 alkyl, C1-C6 alkyloxycarbonyl-C1-C6 alkyl groups, or mixed ethers thereof. In such substituted βCDs, the hydrogen of one or more βCD hydroxy group can be replaced by C1-C3 alkyl, hydroxy-C2-C4 alkyl, or carboxy-C1-C2 alkyl, for example, by methyl, ethyl, hydroxyethyl, hydroxypropyl, hydroxybutyl, carboxymethyl or carboxyethyl. It should be recognized that the term "C1-C6 alkyl" includes straight and branched saturated hydrocarbon radicals, having from 1 to 6 carbon atoms. Examples of βCD ethers include dimethyl-βCD. Examples of βCD polyethers include hydroxypropyl-p-βCD and hydroxyethyl-βCD (see, for example, Nogradi, "Drugs of the Future" 9(8):577-578, 1984; Chemical and Pharmaceutical Bulletin 28: 1552-1558, 1980; Yakugyo Jiho No. 6452 (Mar. 28, 1983); Angew. Chem. Int. Ed. Engl. 19: 344-362, 1980; U.S. Pat. No. 3,459,731; EP-A-0,149,197; EP-A-0, 197,571; U.S. Pat. No. 4,535,152; WO-90/12035; GB-2,189, 245; Szejtli, "Cyclodextrin Technology" (Kluwer Academic Publ. 1988); Bender et al., "Cyclodextrin Chemistry" (Springer-Verlag, Berlin 1978); French, Adv. Carb. Chem. 12:189-260; Croft and Bartsch, Tetrahedron 39:1417-1474, 1983; Irie et al., Pharm. Res. 5:713-716, 1988; Pitha et al., Internat'l. J. Pharm. 29:73, 1986; U.S. Pat. No. 5,134,127 A; U.S. Pat. Nos. 4,659,696 and 4,383,992, each of which is incorporated herein by reference; see, also, U.S. Pat. No. 6,194,395).

In one embodiment, a method of the invention is performed by contacting the pathogen or cells susceptible to infection by the pathogen with a βCD. As used herein, reference to cells being "susceptible" to infection by a sexually transmitted pathogen means that the membranes of the cells contain lipid rafts, to which the pathogen can associate and through which it can traverse the membrane. Cells susceptible to a sexually transmitted pathogen are exemplified by vaginal epithelial cells, which contain lipid rafts that are used by HIV to traverse the cell membrane (see Example 1).

As used herein, the term "sexually transmitted pathogen" refers to any viral or microbial organism that causes a sexually transmitted disease. The term "sexually transmitted disease" refers to a disease that is transmitted through sexual contact with an infected individual. Sexually transmitted diseases and the sexually associated pathogens associated therewith are well known in the art and include, for example, those caused by bacteria such as gonorrhea (Neisseria gonnorrhoeae) and syphilis (*Treponema pallidum*), and infections due to *Chlamydia* spp. such as *C. trachomatis, Calymmatobacterium granulomatis, Ureaplasma urealyticum, Mycoplasma hominus, Gardnerella vaginalis*, and Group B *Streptococcus* spp.; those caused by viruses such AIDS (HIV-1 and HIV-2), genital herpes (Herpes simplex type 2; HSV-2), and infections due to human T lymphotrophic virus type I (HTLV-1), human papillomaviruses, *Cytomegalovirus, Molluscum contagiosum virus*, hepatitis B virus, and possibly HSV-1, HTLV-II, and Epstein-Barr virus; and those due to yeast such as *Candida* spp., for example, *C. albicans*, or to protozoans such as *Trichomona* spp., for example, *T vaginalis* (see Harrison's "Principles of Internal Medicine", supra, 1994).

As disclosed herein, where a sexually transmitted disease is due to infection by a pathogen that traverses a susceptible cell through lipid rafts in the membrane of the cell, the risk of transmission of the pathogen can be reduced by contacting the pathogen or the cell with a βCD (see Examples 2 to 4). As used herein, the term "reducing the risk of transmission of a sexually transmitted pathogen" means that the likelihood that the pathogen will infect a susceptible cell is decreased due to contact of the pathogen or the cell with a βCD as compared to the likelihood of infection of the cell in the absence of βCD treatment. The likelihood of infection of such cells (i.e., untreated or contacted with a βCD) can be determined by examining populations of such cells and determining the levels of infection of the cells by the pathogen using methods as disclosed herein or otherwise known in the art (see Examples 2 to 4).

A method of the invention is performed, for example, by contacting the pathogen or cells susceptible to infection by the pathogen with a βCD. As used herein, the term "contacting," when used in reference to a βCD and the pathogen or cells susceptible to a sexually transmitted pathogen, means that the βCD is placed in sufficient proximity to the pathogen or the susceptible cells such that it prevents the pathogen from entering a cell through lipid rafts or such that it disrupts lipid rafts in the membranes of the susceptible cells. Thus, the βCD can be added to cells in culture, for example, thereby contacting the cells with the βCD; or can be inserted into vagina or rectum of a subject either in a liquid or liquid-like form such as a gel, foam, or the like, or as a suppository, or in combination with a solid substrate such as a condom, thereby contacting the sexually transmitted pathogen or the cells susceptible to the pathogen in vivo.

The significance of detergent-insoluble, glycolipid-enriched membrane domains ("lipid rafts") has been demonstrated, particularly in regard to activation and signaling in T lymphocytes. Lipid rafts can be viewed as floating rafts composed of sphingolipids and cholesterol that sequester glycosylphosphatidylinositol-(GPI)-linked proteins such as Thy-1 and CD59. CD45, a 200 kDa transmembrane phosphatase protein, is excluded from these domains. Human immunodeficiency virus type 1 (HIV-1) particles produced by infected T cell lines acquire the GPI-linked proteins Thy-1 and CD59, as well as the ganglioside GM1, which is known to partition preferentially into lipid rafts. In contrast, despite its high expression on the cell surface, CD45 is poorly incorporated into virus particles. Confocal fluorescence microscopy revealed that HIV-1 proteins colocalized with Thy-1, CD59, GM1, and a lipid raft-specific fluorescent lipid, DiIC16 (see below), in uropods of infected Jurkat cells. CD45 did not colocalize with HIV-1 proteins and was excluded from uropods. Dot immunoassay of TRITON X-100 detergent-extracted membrane fractions revealed that HIV-1 p17 matrix protein and gp41 were present in the detergent-resistant fractions and that ($^3$H)-myristic acid-labeled HIV Gag showed a nine-to-one enrichment in lipid rafts. As disclosed herein, the budding of HIV virions through lipid rafts is associated with the presence of host cell cholesterol, sphingolipids, and GPI-linked proteins within these domains in the viral envelope, indicating preferential sorting of HIV Gag to lipid rafts (see Example 1).

Glycolipid-enriched membrane (GEM) domains are organized areas on the cell surface enriched in cholesterol, sphingolipids, and GPI-linked proteins. These domains have been described as "rafts" that serve as moving platforms on the cell surface (Shaw and Dustin, *Immunity* 6:361-369, 1997). The domains, now referred to as "lipid rafts," exist in a more ordered state, conferring resistance to TRITON X-100 detergent treatment at 4° C. (Schroeder et al., *J. Biol. Chem.* 273:1150-1157, 1998). Many proteins are associated with lipid rafts, including GPI-linked proteins, Src family kinases, protein kinase C, actin and actin-binding proteins, heterotrimeric and small G proteins, and caveolin (see, for example, Arni et al., *Biochem. Biophys. Res. Commun.* 225:8001-807, 1996; Cinek and Horejsi, *J. Immunol.* 149:2262-2270, 1992; Robbins et al., *Mol. Cell. Biol.* 15:3507-3515, 1995; and Sargiacomo et al., *J. Cell. Biol.* 122:789-807, 1993). Saturated acyl chains of the GPI anchor have been shown to be a determinant for the association of GPI-linked proteins with lipid rafts (Rodgers et al., *Mol. Cell. Biol.* 14:5384-5391, 1994; Schroeder et al., *Proc. Natl. Acad. Sci., USA* 91:12130-12134, 1994). Lipid rafts exclude certain transmembrane molecules, specifically the membrane phosphatase CD45 (Arne et al., supra, 1996; Rodgers and Rose, *J. Cell. Biol.* 135: 1515-1523, 1996). Exclusion of CD45 results in the accumulation of phosphorylated signaling molecules in lipid rafts, and T cell activation requires clustering of signaling molecules in these membrane domains (Lanzavecchia et al., *Cell* 96:1-4, 1999).

HIV-1 excludes CD45 from its membrane, despite the abundance of CD45 on the cell surface. This result was in contrast to that observed for other membrane proteins, some of which are expressed at lower levels than CD45, but were efficiently incorporated by the virus (Orentas and Hildreth, *AIDS Res. Hum. Retrovir.* 9:1157-1165, 1993, which is incorporated herein by reference). CD45 is a large, heavily glycosylated, multiply spliced transmembrane protein that has two cytoplasmic tyrosine phosphatase domains. Extracellularly, it may extend as much as 40 nm from the cell surface, while intracellularly it has a large cytoplasmic tail of 707 amino acids. CD45 is one of the most highly expressed leukocyte surface proteins, and as much as 10 to 25% of the lymphocyte cell surface can be covered with CD45. If HIV-1 incorporated host proteins in a random manner, a significant number of CD45 molecules should be present on the virus.

As disclosed herein, CD45 is excluded from HIV-1 particles as a result of virus budding from lipid rafts, which also exclude CD45 (Example 1). HIV-1 incorporates the lipid raft-specific ganglioside, GM1, as well as GPI-linked proteins Thy-1 and CD59. Confocal fluorescence microscopy showed that viral proteins colocalize with Thy-1, CD59, GM1, and 1,19-dihexadecyl-3,3,39,39-tetramethyl indocarbocyanine (DiIC16; Arthur et al., *Science* 258:1935-1938, 1992, which is incorporated herein by reference), a fluorescent dye that partitions to ordered domains in uropods on infected cells. In contrast, CD45 is excluded from these GPI-linked protein-rich membrane projections. Upon membrane fractionation, HIV matrix (MA) and gp41, the transmembrane subunit of envelope (Env), are present in detergent-resistant, GPI-linked protein-rich fractions, confirming their association with lipid rafts. Specifically, myristylated Gag localizes predominantly to the detergent resistant lipid rafts.

These results indicate that HIV-1 budding occurs through lipid rafts, thereby accounting for the cholesterol-rich, sphingolipid-rich virus membrane, which bears GPI-linked proteins such as Thy-1 and CD59, but lacks CD45.

Lipid raft-associated molecules, including the GPI-anchored proteins Thy-1 and CD59 and the ganglioside GM1, colocalized with HIV-1 proteins on the cell surface as determined by confocal fluorescence microscopy (Example 1). Virus phenotyping with MAbs also indicated that these molecules were incorporated into HIV-1 particles. In contrast, CD45 was excluded from HIV-1 protein-rich uropods and was also excluded from the viral membrane. Similarly, DiIC16 colocalized with HIV-1 proteins, while DiIC12, a lipid analog that prefers fluid membrane domains, was excluded from these areas. Dot blot immunoassays of membrane fractions confirmed the presence of HIV-1 gp41 and MA proteins in lipid rafts, and labeling of cells with tritiated myristic acid and immunoprecipitation showed the partitioning of myristylated Gag to lipid rafts.

It was previously reported that HIV-1 acquires CD55 (DAF) and CD59, which inhibit steps in the complement pathway (Marschang et al., *Eur. J. Immunol.* 25:285-290, 1995; Saifuddin et al., *J. Gen. Virol.* 78:1907-1911, 1997). CD55 and CD59 are GPI-linked proteins that are enriched in GEM domains and, together, provide an advantage for the virus by shielding it from lysis and from neutralization by complement. The results disclosed herein confirm and extend the previous observations by demonstrating that HIV-1 incorporates GPI-anchored proteins, which preferentially sort to lipid rafts, and that lipid rafts are the cell membrane microdomains from which HIV-1 buds (Example 1). The high concentration of cholesterol and sphingolipids in lipid rafts explains the high levels of these lipids in the membrane of HIV-1 and supports this model of HIV-1 budding. Interestingly, inhibition of cholesterol synthesis decreases the production of virus from infected cells (Maziere et al., *Biomed. Pharmacother.* 48:63-67, 1994). Since it is unlikely that viral proteins can aggregate individual cholesterol and sphingolipid molecules, the Gag (MA) protein may preferentially interact with existing lipid rafts, where aggregation of Gag (MA) molecules can initiate virus budding. In this manner, sphingolipid-rich and cholesterol-rich lipid rafts can be efficiently taken up by new viruses during budding.

The role of lipid rafts in viral infection can further be extended to viruses other than HIV. For example, selective budding occurs for an influenza virus, fowl plague virus, from ordered lipid domains (Scheiffele et al., *J. Biol. Chem.* 274: 2038-2044, 1999, which is incorporated herein by reference). The requirement for cholesterol and sphingolipids in target membranes for Semliki Forest virus fusion also has been established (Nieva et al., *EMBO J.* 13:2797-2804, 1994; Phalen and Kielian, *J. Cell Biol.* 112:615-623, 1991, each of which is incorporated herein by reference). The interactions of lipid rafts with accessory HIV-1 molecules such as Vif and Nef can have important roles in virus budding, since interactions of myristylated HIV and simian immunodeficiency virus Nef with Lck, which is present in lipid rafts, and its incorporation into virions have been established (see, for example, Collette et al., *J. Biol. Chem.* 271:6333-6341, 1996; Flaherty et al., *AIDS Res. Hum. Retrovir.* 14:163-170, 1998).

The incorporation of Thy-1, CD59, and other GPI-linked proteins into the viral envelope can have a number of consequences for virus infection and pathogenicity. For example, Thy-1, CD59, and CD55 have cell-signaling capabilities, and the transfer of these highly concentrated proteins into the host cell by HIV-1 particles can be involved in triggering an activation signal leading to interleukin-2 production and T cell proliferation. GPI-linked proteins are physically associated with the I-subunit of G proteins, which are important in signal transduction, while other signaling molecules, such as Src family kinases, are associated with lipid rafts (see, for example, Rodgers et al., *Mol. Cell. Biol.* 14:5384-5391, 1994). Delivery of these signal transduction molecules to the host cells by the virus can have important effects on virus infectivity, depending, for example, on the cell type and its state of activation. Among other effects, GPI-linked molecules acting through G proteins can activate integrins such as LFA-1, which can contribute greatly to HIV-1 infectivity and syncytium formation (see Gomez and Hildreth, *J. Virol.* 69:4628-4632, 1995).

A recent model suggests that CD45 is driven out of cap sites that serve as zones for cellular adhesion and activation between a T cell and an antigen-presenting cell (Shaw and Dustin, *Immunity* 6:361-369, 1997). In this model, short, low-affinity molecules such as the T cell receptor are clustered into the cap site, enhancing the two-dimensional affinity of these molecules for their ligands. This same mechanism results in exclusion of CD45 and capping of GPI-linked proteins and lipid rafts into the areas of cell-to-cell contact. Viral protein targeting through association with lipid rafts into cap sites may facilitate virus particle formation at that site on the surface by directing myristylated matrix proteins and accessory molecules.

The exclusion of CD45 from virions may be an important aspect of HIV assembly. Since the cytoplasmic tail of CD45 is so large (more than 700 amino acids), incorporation of CD45 can hinder critical interactions between gp41 and matrix proteins or other molecules. Furthermore, the long, highly negatively charged extracellular domain of CD45, determined to be as long as 41 nm, can sterically hinder viral binding to target cells if it were to be incorporated, considering that a virus particle is only about 100 nm in diameter.

The results disclosed in Example 1 indicate that HIV-1 buds through lipid rafts. During the course of infection, the cell becomes activated and polarization occurs, capping normally dispersed lipid rafts along with GPI-linked proteins and associated intracellular signaling molecules, and membrane areas containing CD45 can be cleared out of the cap site. The newly translated viral Gag precursor protein associated with lipid rafts then can be directed to the capped pole, where assembly and budding occurs. Palmitylated gp41 (gp160) is also directed into lipid rafts, and the interaction of its cytoplasmic tail with MA in lipid rafts can prevent its internalization, allowing for the incorporation of gp160 into virions only at the site of budding (see Egan et al., *J. Virol.* 70:6547-6556, 1996; Yu et al., *J. Virol.* 66:4966-4971, 1992). Individual targeting of Gag and Env to the same site at the membrane can be an important means for delivering these proteins to the site of budding, since Gag and Env are processed and transported in different pathways within the cell. The host membrane then can become the new viral coat, resulting in the incorporation of cholesterol, sphingolipids, Thy-1, and CD59 and in the exclusion of CD45. HIV-1 also acquires functional adhesion molecules from host cells (Orentas and Hildreth, supra, 1993). These host-acquired proteins can significantly affect the biology of HIV-1 (see, for example, Fortin et al., *J. Virol.* 71:3588-3596, 1997).

As described above, budding of HIV-1 particles occurs at lipid rafts, which are characterized by a distinct lipid composition that includes high concentrations of cholesterol, sphingolipids, and glycolipids. Since cholesterol plays a key role in the entry of some other viruses, the role in HIV-1 entry of cholesterol and lipid rafts in the plasma membrane of susceptible cells was investigated (Example 2). A βCD derivative, 2-hydroxypropyl-β-cyclodextrin (2-OH-βCD), was used to deplete cellular cholesterol and disperse lipid rafts. As disclosed herein, removal of cellular cholesterol rendered primary cells and cell lines highly resistant to HIV-1-mediated syncytium formation and to infection by both CXCR4- and CCR5-specific viruses. 2-OH-βCD treatment of the virus or cells partially reduced HIV-1 binding, while rendering chemokine receptors highly sensitive to antibody-mediated internalization, but had no effect on CD4 expression. These effects were readily reversed by incubating cholesterol-depleted cells with low concentrations of cholesterol-loaded 2-OH-βCD to restore cholesterol levels. Cholesterol depletion also made cells resistant to SDF-1-induced binding to ICAM-1 through LFA-1. This may have contributed to the reduction in HIV-1 binding to cells after treatment with the βCD, since LFA-1 contributes significantly to cell binding by HIV-1 which, like SDF-1α, can trigger CXCR4 function through gp120. These results indicate that cholesterol is involved in the HIV-1 co-receptor function of chemokine receptors and is required for infection of cells by HIV-1 (see Example 2).

As discussed above, cholesterol, sphingolipids, and GPI-anchored proteins are enriched in lipid rafts (see Simons and Ikonen, *Nature* 387:569-572, 1997). The high concentration of cholesterol and sphingolipids in lipid rafts results in a tightly packed, ordered lipid domain that is resistant to non-ionic detergents at low temperature. The structural protein caveolin causes formation of flask-like invaginations (caveolae) in the cell membrane with a lipid composition very similar to that of lipid rafts (Schnitzer et al., *Science* 269:1435-1439, 1995). Signaling molecules, including Lck, LAT, NOS, and G protein I subunit, are localized to rafts on the intracellular side of the membrane, and are targeted by lipid modifications such as palmitylation, myristylation, or both. In comparison, many other transmembrane proteins do not show a preference for lipid rafts; for example, CD45 and E cadherin are excluded from these areas. Certain lipid modified transmembrane proteins such as the HA molecule of influenza virus localize to lipid rafts.

Chemokine receptors (CRs), which serve as HIV co-receptors, are G-coupled proteins with seven membrane spanning domains, and belong to the large family of serpentine receptors. The large number of membrane interacting domains indicates that CRs can be more profoundly affected by the lipids in the surrounding milieu than can a single pass transmembrane protein. For example, membrane cholesterol is essential in the binding of the neuropeptide galanin to its G-coupled seven membrane spanning receptor, GalR2. Precedence for cholesterol effects on transmembrane protein function has been established by demonstrating that cholesterol is required for ligand binding by two serpentine receptors, the oxytocin receptor and the brain cholecystokinin receptor (Gimpl et al., *Biochemistry* 36:10959-10974, 1997), and the role of cholesterol in receptor function has been attributed to association of the oxytocin receptor with lipid rafts (Gimpl and Fahrenholz, *Eur. J. Biochem.* 267:2483-2497, 2000). Similarly, as discussed above, the Semliki Forest virus (SFV) spike protein requires cholesterol and sphingolipids on target membranes for infection. Interestingly, the presence of chemokine receptor 5 (CCR5) in lipid rafts on MCF7 cells correlates with its polarized distribution in chemotactic cells, but the functional correlation between CCR5 and lipid rafts has not been well studied. A role for lipid rafts in CXCR4 signaling has not been established.

As disclosed herein, HIV-1 buds selectively from lipid rafts of infected T cells (Example 1). In addition, to SFV, measles viruses, influenza viruses, and polioviruses assemble by raft association and, in the case of influenza virus, to bud from rafts (see, for example, Marquardt et al., *J. Cell Biol.* 123:57-65, 1993; Manie et al., *J. Virol.* 74:305-311, 2000; Zhang et al., *J. Virol.* 74:4634-4644, 2000, each of which is incorporated herein by reference). The involvement of lipid rafts in HIV-1 biology beyond its role in virus budding has been further examined. As further disclosed herein, partial depletion of cholesterol from cell membranes using a βCD inhibited HIV-1-induced syncytium formation in cell lines and primary T cells (Example 2). βCD treatment of cells also increased CR internalization induced by monoclonal antibody (MAb) binding. Primary cells and cell lines were rendered resistant to infection CXCR4-specific and CCR5-specific HIV-1 strains by treatment with 2-OH-βCD (Example 2). The effects observed were not due to loss of cell viability after treatment with the βCD, and demonstrate that intact lipid rafts and cholesterol are required for HIV-1 infection and syncytium formation.

Since cholesterol is highly concentrated in lipid rafts and has been implicated in the entry of other viruses, the effect of lipid raft dispersion by cholesterol depletion on HIV-1 infection and syncytium formation was examined. As disclosed herein, cholesterol is required for both HIV-1 induced cell-cell fusion as well as infection by free virus particles, similar to that reported for SFV, and contact of HIV-1 with βCD rendered the virus non-infectious. In the case of SFV, it appears that the cholesterol dependence can be attributed to the envelope spike protein. Another alphavirus, Sindbis virus, also requires cholesterol in target membranes for infection (Lu et al., *J. Virol.* 73:4272-4278, 1999). In vitro assays determined that cholesterol and sphingolipids are required in liposomes for fusion with Sindbis virus at low pH, even in the absence of receptor (Smit et al., *J. Virol.* 73:8476-8484, 1999). Those studies established a clear requirement for cholesterol in membrane fusion for the alpha viruses, and the present results indicate a similar role for cholesterol in HIV-1 fusion. The importance of cholesterol for HIV-induced membrane fusion is also supported by studies showing that cholesterol in large unilamellar vesicles enhanced the membrane fusion activity of an HIV-1 gp41-derived peptide (Pereira et al., *AIDS Res. Hum. Retrovir.* 13:1203-1211, 1997).

Glycolipids are important components of lipid rafts and the role of host glycolipids in HIV infection is being investigated. Inhibition of sphingolipid synthesis by inhibitors such as PPMP (1-phenyl-2-hexadecanoylamino-3-morpholino-1-propanol) reduces HIV infection of CD4+ human cells by 50% (Puri et al., *Biochem. Biophys. Res. Commun.* 242:219-225, 1998). Moreover, CD4+ non-human cells were made susceptible to gp120-gp41 mediated cell fusion by the addition of human erythrocyte glycolipids (Puri et al., supra, 1998). CD4-induced binding of gp120 to glycosphingolipids Gb3 and GM3 from reconstituted lipid raft microdomains also has been demonstrated (Hammache et al., *J. Virol.* 73:5244-5248, 1999). Those results suggest that glycolipids, which are enriched in lipid rafts, can also serve as cofactors in determining viral tropism. Glycolipid-enriched membrane domains (lipid rafts) may serve as platforms for organizing CD4, CRs, and gp120/41 into fusion complexes (Hug et al., *J. Virol.* 74:6377-6385, 2000).

The results disclosed herein support a model for preferential HIV-1 interactions with lipid rafts as sites for virus entry (Example 2). SV40 also enters cells at lipid rafts (caveolae) even though its receptor appears to be MHC class I. The virus may bind to other regions of the cell membrane, but translocate to caveolae for entry. In addition, several bacterial toxins target lipid rafts as well. For example, the bacterial toxins aerolysin and *Clostridium septicum* alpha toxin bind to GPI-anchored proteins, which are highly enriched in lipid rafts, and the *Vibrio cholerae* toxin binds to GM1. Cholera toxin oligomerization and pore formation in liposomes is promoted by cholesterol and sphingolipids (Zitzer et al., *J. Biol. Chem.* 274:1375-1380, 1999), and host derived GPI-anchored proteins acquired by HIV-1 budding from lipid rafts renders the virus susceptible to neutralization by aerolysin (Nguyen et al., *Mol. Microbiol.* 33:659-666, 1999).

The reduction of virus binding to cells treated with βCD likely involves more than βCD effects on CRs, since adhesion molecules also are involved in virus binding to cells (Liao et al., *AIDS Res. Hum. Retrovir.* 16:355-366, 2000, which is incorporated herein by reference). The affinities of adhesion molecules, including integrins LFA-1 and IVβ3, for their ligands are diminished by treatment of cells with βCD. Conversely, the addition of cholesterol increases binding of I5β1 integrin to fibronectin, as well as increasing its localization to focal adhesions and interactions with the cytoskeleton. As disclosed herein, cholesterol depletion rendered CXCR4 sensitive to MAb-induced internalization not seen on control cells (Example 2). This result indicates that cholesterol is involved in maintaining stable expression of CXCR4. Furthermore, cells treated with βCD did not respond to SDF-1 in LFA-1-mediated cell adhesion assays. This result demonstrates that CXCR4, which normally regulates LFA-1 function, did not do so after cholesterol depletion. Thus disruption of integrin function on βCD-treated cells can significantly diminish virus binding given the demonstrated role of these molecules in HIV binding to cells.

Multiple extracellular loop domains of CXCR4 and CCR5 are believed to be involved in CR-gp120 binding and the subsequent conformational changes that lead to HIV-1 fusion. Mouse CCR5 extracellular loop (ECL) loop swapping with human CCR5 revealed that all three loops are involved in functional interaction with the HIV-1 envelope (Bieniasz et al., *EMBO J.* 16:2599-2609, 1997). Env interactions with multiple ECLs of the co-receptor suggests that binding occurs in a groove or pocket at the level of the plasma membrane. Accordingly, a small molecule blocked gp120 interaction with CCR5 in a pocket formed between transmembrane helices 1, 2, 3, and 7. For CXCR4, antagonist peptide T22 blocked HIV-1 infection by interacting with the N-terminus and at least ECL1 and ECL. Since CRs can project no further than a few nm above the plane of the membrane, gp120-CR interactions may bring their respective membranes into close opposition to each other. Close membrane contact is required for lipid intermixing between the two membranes after the triggering of conformational changes in gp41. The requirement for conformational integrity of CR TM domains is evidenced by the finding that structural analogs of TM domains of CXCR4 and CCR5 inhibit signaling and HIV infection. The insertion of these peptides is believed to disrupt the interactions of the transmembrane helices in the CR, knocking out both its ability to transmit signals and support HIV fusion. Thus changes in CR conformation in either their TM domains or ECLs can profoundly affect their ability to serve as HIV-1 co-receptors. The present results indicate that cholesterol is involved in maintaining functional conformations of both CCR5 and CXCR4 (Example 2), a suggestion that is supported by results using the serpentine receptors, the oxytocin and cholecystokinin receptors (Gimpl et al., supra, 1997), where the receptor function was strictly dependent on cholesterol, and from ligand binding studies suggesting that depletion of cholesterol from the cell membrane alters the conformation of these receptors.

Clustering of CXCR4 by cytoskeletal rearrangements can be important in HIV-1 cell entry and promoting chemotaxis of CD4 and CD8 cells (Hildreth and Orentas, *Science* 244:1075-1078, 1989, which is incorporated herein by reference; see, also, Yang et al., *J. Biol. Chem.* 274:11328-11333, 1999). Lipid raft aggregation induced by a chemotactic stimulation produces similar cellular rearrangements (Manes et al., *EMBO J.* 18:6211-6220, 1999). That redistribution of proteins, including CCR5 and the T cell receptor, into lipid rafts appears is a critical trigger for cell function is supported by the finding that the removal of cholesterol inhibits chemotaxis and cell polarization mediated through CCR5 (Nieto et al., *J. Exp. Med.* 186:153-158, 1997; Lanzavecchia et al., supra, 1999). Inhibition of HIV infection by cholesterol depletion may reflect a similar requirement for these processes in HIV-1 infection.

Enhanced MAb-induced internalization of CR occurred after βCD depletion of cellular cholesterol (Example 2). Interestingly, the opposite effect was observed in studies on the transferrin and epidermal growth factor receptors, where βCD treatment reduced the rate of internalization through clathrin coated pits. Previous studies on CXCR2 and CXCR4 internalization induced by SDF-1I and PMA stimulation have shown that this process may be mediated by clathrin coated vesicles. Since βCD depletion of cholesterol appears to inhibit coated vesicle internalization, MAb-induced CR internalization in BCD-treated cells may occur through a distinct pathway, for example, similar to the displacement of caveolin from caveolae to the Golgi apparatus that occurs after cholesterol oxidase treatment of cells, which produces membrane effects similar to cholesterol removal. Cholesterol depletion also may alter CR interactions with other proteins at the cell membrane that are necessary for stable membrane expression.

Whether cholesterol is needed for conformational stability, stable membrane expression, lipid raft mediated cell signaling, or all of the above is not yet clear. Cholesterol removal does not strictly affect lipid rafts alone, but also can affect cell signaling and other cellular functions. However, the results on HIV-1 induced syncytium formation, which only requires expression of envelope protein and viral co-receptors at appropriate levels, indicate that intact lipid rafts and cholesterol play a critical role in the early steps of virus binding and fusion (Examples 1 and 2). These results extend previous reports showing fully reversible inhibition of HIV infection by depletion cholesterol from susceptible cells with βCD (Manes et al., *EMBO J.* 1: 190-196, 2000). However, the latter studies were based primarily on transfected epithelial cell lines (293, HeLa), and did not examine the effect of βCD treatment on LFA-1, CD4 or CR expression, and in contrast to the present results, did not detect any reduction in HIV binding after βCD treatment, perhaps because LFA-1-negative cells were used in the binding assay.

HIV-1 prevention strategies must consider both cell-free and cell-associated virus because both HIV-1 virions and HIV-infected cells are present in the semen and cervical mucus of infected individuals. Antibodies that target HIV-1 virions can prevent vaginal transmission of cell-free virus in macaques. However, since cell-associated transmission has not been reliably demonstrated in these model systems, no strategies to prevent such transmission have been tested. A model of vaginal transmission using human peripheral blood leukocyte (HuPBL) reconstituted, severe combined immunodeficient (SCID) mice (HuPBL-SCID mice), in which cell-associated HIV-1 transmission occurs and is mediated by transepithelial migration of HIV-infected cells, is described (Khanna et al., 2001), and was used to demonstrate that topically applied βCD blocks transmission of cell-associated HIV-1 (Example 3). These results also demonstrate that the HuPBL-SCID model of vaginal HIV-1 transmission is useful for investigating cell-associated transmucosal HIV-1 transmission, and for screening reagents for their potential efficacy in preventing sexual transmission of pathogens such as HIV. The HuPBL-SCID mouse model provides a means to screen large numbers of animals to determine the statistical robustness of observations made using a pathogen of interest. Thus, while the utility of the model is exemplified by addressing the role of cell-associated transmission of HIV-1, it will be recognized that the model also is useful for examining other sexually transmitted pathogens that share features of HIV-1 transmission clinically, including, for example, the transmission of viruses that use CCR5 as a co-receptor.

The results demonstrating that HIV-1 transmission to vaginal cells by treatment with βCD were extended to another sexually transmitted enveloped virus, HSV-2. As disclosed herein, contact of HSV-2 virus with 2-OH-βCD significantly reduced vaginal infectiousness of the virus in a mouse genital herpes model system (see Example 4; see, also, Sherwood et al., Nature Biotechnol. 14:468-471, 1996; which is incorporated herein by reference). These results demonstrate that βCD is useful for reducing the risk of transmission of a variety of sexually transmitted pathogens, including sexually transmitted enveloped viruses.

The migration of HIV-infected cells and the movement of assembled virus particles out of infected donor cells are critical to HIV-1 transmission. As disclosed herein, HIV-1 budding occurred selectively through lipid rafts on the cell surface (Examples 1 and 2). In addition, the ability of lipid rafts to act as adhesion platforms facilitates cell-cell interactions and migration, which may be important for cell-to-cell transfer of virus and for entry of infected cells through genital tract epithelia, respectively (Krauss and Altevogt, J. Biol. Chem. 274:36921-36927, 1999; Manes et al., supra, 1999). βCDs, which are water soluble compounds that disrupt lipid rafts by removing cholesterol from cellular membranes, interrupt cellular migration (Okada et al., J. Pharm Exp. Ther. 273:948-954, 1995) and inhibit syncytium formation of HIV-1 infected cells (see Example 2).

The HuPBL-SCID mouse model was used to examine the ability of the βCD derivative, 2-OH-βCD, to interrupt cell-associated transmission of HIV-1. As disclosed herein, intravaginal administration of a βCD prior to challenge by HIV-1 infected cells efficiently blocked virus transmission and induced minimal, if any, damage to the vaginal mucosa (Example 3). In addition, a mouse genital herpes model system was used to demonstrate that βCD treatment can reduce the risk of transmission of cell-free HSV-2 (Example 4). These results demonstrate that animal models for vaginal transmission of sexually transmitted diseases can be used to screen βCD derivatives in a cost-effective way, thus providing a means to identify βCDs that can reduce the risk of transmission of sexually transmitted pathogens and that do not cause undue toxicity to normal healthy tissue.

Several mechanisms have been proposed by which HIV-1 is able to traverse the epithelium of the genitourinary tract to establish productive infection in lymph nodes. For example, HIV-1 can be transmitted from infected lymphocytes to epithelial cells, or through the epithelium, which serves as a conduit through which virus is transcytosed, presumably to cells within the lamina propria that are susceptible to productive infection. Intravaginal inoculation of rhesus macaques with SIV demonstrated rapid association of the virus with dendritic cells adjacent to or between the epithelial cells lining the genitourinary tract (Miller and Hu, J. Infect. Dis. 179(Suppl. 3):S413-417, 1999), or to quiescent T cells similarly placed in the reproductive tract (Zhang et al., Science 286:1353-1357, 1999). All of these mechanisms of transmission involve exposure of free virus to the extracellular environment, providing an opportunity, albeit a brief one, for virus specific intervention strategies to be effective at the mucosal surface. Of additional concern, however, is the possibility that lymphocytes or macrophages from the infected donor could migrate directly through the epithelium of the genitourinary tract to infect lymphocytes in lymph nodes draining the genitourinary tract. As such, anti-HIV antibodies or other virion-specific strategies, while important and perhaps necessary for a protective effect, may not be sufficient to prevent transmission of the virus.

Migrating cells carrying HIV have been referred to "Trojan horse" leukocytes because of their ability to hide the virus from virus-specific defenses that may be present within the genitourinary tract (Anderson and Yuni, New Engl. J. Med. 309:984-985, 1983). While considerable effort has been directed to identifying virus-specific intervention strategies effective against sexual transmission of human and simian immunodeficiency viruses, there has been little effort to identify strategies for interrupting migration of infected cells to regional lymph nodes. Use of a mouse model of vaginal transmission demonstrated vaginal transmission of HIV-1 using infected-cell inocula (Example 3). The HuPBL-SCID model is unique in that the processes of cell-associated HIV-1 transmission can be examined in the absence of the possibility of that cell-free virus is mediating transmission. In fact, the amount of infectious virus produced by the number of infected cells in the inocula used in the present study would be predicted to be dramatically less than $1 \times 10^6$ $TCID_{50}$ of free virus that failed to infect (Burkhard et al., AIDS Res. Hum. Retrovir. 13:347-355, 1997).

In the HuPBL-SCID mouse system, HIV-1-infected PBMC can migrate through cervix-like epithelium to regional lymph nodes (Example 3). As such, the mice can be used to evaluate strategies for effectively blocking cell-associated HIV-1 transmission. To date, cell-associated SIV has not been successfully transmitted by the vaginal route in a macaque model, although both cell-free and cell-associated HIV-1 have been transmitted by viral inoculations at the cervical os of chimpanzees. Similarly, both cell-free and cell-associated feline immunodeficiency virus have been transmitted in cat models of vaginal infection.

In the HuPBL-SCID mice, only CCR5-utilizing HIV-1 can be transmitted and establish infection in the HuPBMC that were transplanted intraperitoneally into the mice. It is unclear whether this preferential transmission reflects preferential movement of CCR5-utilizing virus-infected cells across the mucosal barrier, or an enhanced ability of these viruses to continue productive infection in the unactivated HuPBMC residing in the peritoneal cavity seven days after human cell transplantation. Nevertheless, this finding parallels the observation that viruses that can use CCR5 as a co-receptor for entry are preferentially transmitted in the clinical setting.

Unlike other model systems of vaginal transmission, the HuPBL-SCID mouse model of transmission is dependent upon the movement of virus-infected cells to sites at which other human cells exist, in this case the peritoneal cavity of the infected mice. Human cells transplanted into the peritoneum do not appear to migrate to the vaginal mucosa or sub-mucosa. As such, the inability of free virus to be transmitted in this system may simply reflect a poor migratory ability of free virus and the absence of human target cells within and beneath the vaginal mucosa. Thus, the results disclosed herein do not indicate that free virus is not transmitted in the clinical setting but, instead, demonstrate that infected-cell migration through cervical epithelium must be considered in any intervention strategy.

The migration of mononuclear cells through murine vaginal epithelium has been documented (see, for example, Ibata et al., *Biol. Reprod.* 56:537-543, 1997; Zacharapoulos et al., *Curr. Biol.* 7:534-537, 1997). The results disclosed herein reinforce the notion that the single layer of columnar epithelial cells present on the surface of the cervix is more susceptible to transmigration of HIV-infected PBMC and, conversely, that the stratified squamous epithelium lining the normal vagina is less vulnerable to transepithelial transmission, presumably by reducing the efficacy of transepithelial migration. Progesterone treatment of the mice effectively converted the vaginal stratified squamous epithelium into a cervix-like columnar epithelium, thus greatly increasing the surface area within the vagina that is covered with columnar epithelium.

The HuPBL-SCID model of vaginal transmission has allowed confirmation that a βCD derivative is highly effective at interrupting vaginal transmission of cell-associated HIV-1. Application of the βCD to the vaginal mucosa prior to inoculation with HIV-1 infected cells dramatically reduced transmission of cell-associated virus (Example 3). βCDs are cyclic, water-soluble carbohydrates that are comprised of seven glucose units and have been used clinically as a food additive (Toyoda et al., *Food Chem. Toxicol.* 35:331-336, 1997) and as a molecular complexing agent that can increase the solubility and stability of some poorly soluble drugs (Sharma et al., *J. Pharm. Sci.* 84:1223-1230, 1995). As disclosed herein, βCD applied to the vaginal mucosa was substantially less toxic than a sub-clinical concentration of the widely used spermicide nonoxynol-9 (see Example 3).

Migration through the epithelium likely involves, as an initial step, interaction between lymphocytes and/or macrophages and epithelial cells. Clustering of lipid rafts on cell membranes results in enhancement of cell-cell interactions and migration, and disruption of the rafts with βCD diminishes cell binding and migration. Moreover, the production of HIV-1 virions from such cholesterol-depleted cells is dramatically decreased and these virions are significantly less infectious. The results disclosed herein demonstrate that the HuPBL-SCID mice of vaginal transmission of cell-associated virus provides a simple and inexpensive system to identify agents that can be used in vaginal products for preventing sexual transmission of HIV-1 (Example 3).

As disclosed herein, 2-OH-βCD significantly blocked vaginal transmission of cell-associated HIV-1 and of cell-free transmission of HSV-2 (Examples 3 and 4). Since this agent is currently used for human administration, it will be recognized that 2-OH-βCD can be used alone, or in combination with other agents such as a contraceptive or antibiotic, to reduce the risk of transmission of sexually transmitted diseases. Accordingly, the present invention also provides methods for reducing the risk of transmission of a sexually transmitted pathogen to or from a subject. As such, a method of the invention can be performed with respect to the infected individual, thus reducing the risk that the subject will transmit the disease to an uninfected subject, or can be performed with respect to an uninfected individual, thus protecting the subject from an infected individual, who may or may not know he or she is infected. Where the method is used to prevent transmission from an infected individual to an uninfected individual, the pathogen or cells susceptible to infection by the pathogen can be contacted with the βCD in the infected subject, in the uninfected subject, or in both. The subject can be any subject susceptible to a sexually transmitted disease, and generally is a vertebrate subject, particularly a mammal, and preferably a human.

A method of the invention can be performed, for example, by contacting the sexually transmitted pathogen or cells susceptible to infection by the pathogen in an uninfected subject with a pharmaceutical composition comprising a βCD, thereby reducing the risk of the subject becoming infected with the sexually transmitted the pathogen. It should be recognized that a method of the invention can reduce the risk of transmission of various sexually transmitted diseases. As such, even where a subject already is infected with one or more sexually transmitted pathogens, a method of the invention can reduce the risk of infection by other sexually transmitted pathogens. A method also can be performed, for example, by contacting the pathogen or the cells susceptible to infection by the pathogen in a subject having a sexually transmitted disease with a pharmaceutical composition comprising a βCD, thereby reducing the risk of transmission of the sexually transmitted disease by the subject to another individual.

The present invention also provides compositions useful for reducing the risk of transmission of sexually transmitted disease. A composition of the invention contains a βCD, which can be in a form suitable for topical administration to a subject, particularly intravaginal or intrarectal use, including a suppository, a bioadhesive polymer, or a vaginal disk, which can provide timed release of the βCD (see, for example, U.S. Pat. Nos. 5,958,461 and 5,667,492, each of which is incorporated herein by reference; see, also, Sherwood et al., supra, 1996); or can be formulated in combination with a solid substrate to produce a condom, diaphragm, sponge, tampon, a glove or the like (see, for example, U.S. Pat. Nos. 6,182,661 and 6,175,962, each of which is incorporated herein by reference), which can be composed, for example, of an organic polymer such as polyvinyl chloride, latex, polyurethane, polyacrylate, polyester, polyethylene terephthalate, poly(ethylene-co-vinyl acetate); polymethacrylate, silicone rubber, a silicon elastomer, polystyrene, polycarbonate, a polysulfone, or the like (see, for example, U.S. Pat. No. 6,183,764, which is incorporated herein by reference; see, also, Sherwood et al., supra, 1996).

For topical administration, the βCD can be formulated in any pharmaceutically acceptable carrier, provided that the carrier does not affect the activity of the βCD in an undesirable manner. Thus, the composition can be, for example, in the form of a cream, a foam, a jelly, a lotion, an ointment, a solution, a spray, or a gel (see U.S. Pat. No. 5,958,461, which is incorporated herein by reference). In addition, the composition can contain one or more additional agents, for example, an antimicrobial agent such as an antibiotic or an antimicrobial dye such as methylene blue or gentian violet (U.S. Pat. No. 6,183,764); an antiviral agent such as a nucleoside analog (e.g., azacytidine), a zinc salt (see U.S. Pat. No. 5,980,477, which is incorporated herein by reference), or a cellulose phthalate such as cellulose acetate phthalate or a hydroxypropyl methylcellulose phthalate (see U.S. Pat. No. 5,985,313, which is incorporated herein by reference); a contraceptive (see U.S. Pat. No. 5,778,886, which is incorporated herein by reference); a lubricant, or any agent generally useful to a sexually active individual, provided the additional agent, either alone or in combination, does not affect the activity of the βCD or, if it affects the activity of the βCD, does so in a predictable way such that an amount of βCD that is effective for reducing the risk of transmission of a sexually transmitted pathogen can be determined.

A pharmaceutically acceptable carrier useful in a composition of the invention can be aqueous or non-aqueous, for example alcoholic or oleaginous, or a mixture thereof, and can contain a surfactant, emollient, lubricant, stabilizer, dye, perfume, preservative, acid or base for adjustment of pH, a solvent, emulsifier, gelling agent, moisturizer, stabilizer, wetting agent, time release agent, humectant, or other component commonly included in a particular form of pharmaceutical composition. Pharmaceutically acceptable carriers are well known in the art and include, for example, aqueous solutions such as water or physiologically buffered saline or other solvents or vehicles such as glycols, glycerol, oils such as olive oil or injectable organic esters. A pharmaceutically acceptable carrier can contain physiologically acceptable compounds that act, for example, to stabilize or to increase the absorption of the βCD, for example, carbohydrates, such as glucose, sucrose or dextrans, antioxidants, such as ascorbic acid or glutathione, chelating agents, low molecular ++weight proteins or other stabilizers or excipients.

The pharmaceutical composition also can comprise an admixture with an organic or inorganic carrier or excipient suitable for intravaginal or intrarectal administration, and can be compounded, for example, with the usual non-toxic, pharmaceutically acceptable carriers for tablets, pellets, capsules, suppositories, solutions, emulsions, suspensions, or other form suitable for use. The carriers, in addition to those disclosed above, can include glucose, lactose, mannose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening or coloring agents and perfumes can be used, for example a stabilizing dry agent such as triulose (see, for example, U.S. Pat. No. 5,314,695).

The βCD also can be incorporated within an encapsulating material such as into an oil-in-water emulsion, a microemulsion, micelle, mixed micelle, liposome, microsphere or other polymer matrix (see, for example, Gregoriadis, *Liposome Technology*, Vol. 1 (CRC Press, Boca Raton, Fla. 1984); Fraley, et al., *Trends Biochem. Sci.*, 6:77 (1981), each of which is incorporated herein by reference). Liposomes, for example, which consist of phospholipids or other lipids, are nontoxic, physiologically acceptable and metabolizable carriers that are relatively simple to make and administer. "Stealth" liposomes (see U.S. Pat. Nos. 5,882,679; 5,395,619; and 5,225,212, each of which is incorporated herein by reference) are an example of such encapsulating materials particularly useful for preparing a pharmaceutical composition of the invention, and other "masked" liposomes similarly can be used, such liposomes extending the time that the βCD remains at the site of administration.

The composition generally is used at or about the time of sexual activity, and usually is used prior to initiating sexual contact. The manner of use will depend, in part, on the form of the composition, for example, whether the composition is in a liquid or liquid-like form such as a jelly, a douche, a cream or the like, or whether the βCD is formulated with a solid substrate such as a sponge, diaphragm, tampon, pessary, condom or the like. When formulated as such a composition, the βCD can be impregnated into an absorptive material such as a sponge or tampon, or coated onto the surface of a relatively impermeable solid substrate such as a condom or diaphragm, or on medical gloves, thus providing a means to contact the βCD with the pathogen or cells in a subject that are susceptible to infection.

The amount a βCD in a composition can be varied, depending on the type of composition, such that the amount present is sufficient to reduce the ability of the pathogen to be sexually transmitted. An effective amount of a βCD can block infection of susceptible cells by a sexually transmitted pathogen such as free HIV, or cell-associated HIV present in a secretion, or by uptake of the pathogen due to binding to otherwise non-susceptible cells, which then transfer the sexually transmitted pathogen to susceptible cells. An example of such an amount is about 1 to 100 mM, generally about 5 to 30 mM, when administered in an ointment, gel, foam, spray or the like, our about 0.1 to 2 grams, generally about 0.25 to 0.75 grams, when administered as a suppository or in combination with a solid substrate. An effective amount of a βCD also can be measured in a weight:weight (w:w) or weight:volume (w:v) amount, for example, about 0.1% to 3% w:w with respect to a solid substrate or about 0.1% to 3% w:v with respect to a pharmaceutically acceptable carrier. In addition, an amount of a βCD sufficient to reducing the risk of transmission of a sexually transmitted disease can be determined using routine clinical methods, including Phase I, II and III clinical trials.

The following examples are intended to illustrate but not limit the invention.

EXAMPLE 1

HIV-1 Selectively Buds From Lipid Rafts

This example demonstrates that HIV-1 budding occurs through lipid rafts, thereby accounting for the cholesterol-rich, sphingolipid-rich virus membrane, which bears GPI-linked proteins such as Thy-1 and CD59, but lacks CD45.

Cells and Antibodies

Jurkat cells were obtained from the American Type Culture Collection (Rockville Md.) and maintained in complete medium, cRPMI, consisting of RPMI 1640 (Gibco BRL/Life Technologies; Gaithersburg Md.) containing 10% fetal calf serum (FCS; HyClone; Logan Utah) and 10 mM HEPES. Monoclonal antibodies (MAbs) to Thy-1 (5E10) and CD59 (p282/H19) were obtained from Pharmingen (San Diego Calif.). Mouse MAb against HIV p17 was obtained from Advanced Biotechnologies, Inc. (Columbia Md.). Goat anti-cholera toxin B (CTB) MAb was purchased from Calbiochem (La Jolla Calif.). Rabbit anti-GM1 polyclonal antibody was purchased from Metraya, Inc. (Pleasant Gap Pa.). Biotinylated human anti-HIV polyclonal antibodies were produced from pooled human HIV 1 sera. Soluble recombinant CD4-immunoglobulin Fc chimera (CD4Ig) was obtained from (Genentech; South San Francisco Calif.). Control mouse myeloma immunoglobulin G1 (IgG1) and rabbit anti-mouse IgG (Fc specific) were purchased from Jackson Immunoresearch (West Grove Pa.). Fluorescein isothiocyanate (FITC)-conjugated sheep anti-human IgG was purchased from Cappel Research Products (Durham N.C.). MAbs to major histocompatibility complex I (MHCI) antigen (MHM.5), HIV-1 Gag (Gag.M1), and CD45 (H5A5) were produced as previously described, and were purified from ascites fluids (Ellis et al., *Hum. Immunol.* 13:13-19, 1985; Hildreth and August, *J. Immunol.* 134:3272-3280, 1985, each of which is incorporated herein by reference).

Virus Production

HIV-1$_{RF}$ was used to chronically infect Jurkat cells. Viruses used for the capture assay were produced by washing $1 \times 10^6$ to $2 \times 10^6$ chronically infected cells with phosphate-buffered saline (PBS), resuspending cells in complete medium, and culturing for 1 to 3 days before collecting culture supernatants. Virus production was measured by p24 enzyme-linked immunosorbent assay (ELISA) after detergent lysis of supernatant.

Flow Cytometry

Flow cytometry was performed as previously described (Orentas and Hildreth, supra, 1993). Briefly, $2\times10^5$ cells in 100 ml of PBS containing 5% normal goat serum (NGS) were added to 100 ml of MAb (1 to 5 mg) and incubated for 30 min on ice. Cells were washed with PBS, resuspended in 100 ml of PBS plus 5% NGS containing 2 mg of FITC-goat anti-mouse IgG (FITC-GAM), and incubated 1 hr on ice. Cells were then washed with PBS and fixed with 2% paraformaldehyde, followed by analysis on an EPICS Profile II (Coulter; Hialeah Fla.) flow cytometer.

Virus Phenotyping

Virus phenotyping was carried out as previously described with some minor differences (Orentas and Hildreth, supra, 1993). Briefly, Costar ELISA plates (Costar; Cambridge Mass.) were coated for 4 hr at 37° C with 1.5 mg of rabbit anti-mouse IgG (Fc fragment specific) per well in 50 mM Tris (pH 9.5). The wells were blocked with 3% bovine serum albumin (BSA) in PBS for 2 hr at 37° C. before adding 1 to 2 mg of the MAbs. The plates were then incubated overnight at room temperature before washing them six times with PBS-0.05% Tween 20. Viral supernatants were collected and clarified through 0.45 Tm (pore-size) filters. The viral supernatants at 466 ng/ml of p24 were added to the antibody-coated wells and incubated at 37° C. for 1.5 hr before washing them six times with RPMI. The bound viruses were then lysed with 1% Triton X-100 in cRPMI for 1 hr at 37° C. Detergent-solubilized viral proteins were transferred to a second plate to measure released p24 in a standard p24 ELISA.

Cell Capture Assay

Costar ELISA plates were coated overnight at room temperature with 1.0 mg of GAM IgG (Fc specific) per well in 50 mM Tris (pH 9.5). Wells were blocked with 3% BSA in PBS for 1 hr at 37° C. before adding 1 to 2 mg of the MAbs. Plates were then incubated for 2 hr at 37° C. before washing them three times with RPMI. Wells were blocked again with 5% NGS in PBS for 1 hr at 37° C. before washing them three times with RPMI. Jurkat cells ($10^7$) were labeled with horseradish peroxidase (HRP; Sigma) at 1 mg/ml in cRPMI for 30 min at 37° C., washed once with cRPMI, then resuspended in cRPMI to make $2.5\times10^6$ cells/ml. Cells (100 ml) were added to the wells and allowed to settle for 2 hr at 37° C. Wells were washed three times with Hanks balanced salt solution (Gibco BRL), then treated with lysis-substrate buffer (1% Triton X-100, 0.015% $H_2O_2$, 0.24 mg of tetramethylbenzidine per ml, 0.2M sodium acetate-citric acid; pH 4.0) for 20 min before the addition of 0.5 M $H_2SO_4$ to stop the reaction. Absorbances at a 450-nm wavelength were determined on a plate reader, and cell number values were extrapolated from a linear curve.

β-Cyclodextrin Treatment and Virus Precipitation

Infected Jurkat cells ($3\times10^6$) were treated with 20 mM hydroxypropyl-β-cyclodextrin (2-OH-βCD; Cyclodextrin Technologies Development, Inc.; Gainesville Fla.) in 3 ml of cRPMI or with cRPMI alone for 1 hr at 37° C. Cells were washed with PBS, then allowed to produce virus in 3 ml of cRPMI at 37° C. for 2 hr. Viral supernatants were clarified through a 0.45 Tm filter, and 100 ml was added to 100 ml of MAb (10 mg/ml) in 5% NGS-PBS, and the mixture was incubated for 1 hr on ice. Pansorbin (SaC) (50 mg; Calbiochem; San Diego Calif.) was added to the solution and incubated for 20 min on ice. Complexes were washed sequentially with 10X and 1X PBS. Precipitated virus was lysed with 400 ml of 1% Triton X-100 in cRPMI. Lysates were diluted, and p24 was quantitated by standard p24 ELISA.

Cholera Toxin Capture of HIV-1

HIV-$1_{RF}$ viral supernatant from an infected Jurkat cell line was collected and clarified through a 0.45 Tm filter. Virus supernatant (100 ml) was added to 100 ml of CTB (Calbiochem) dilutions (0 to 20 mg/ml) in cRPMI. The mixtures were incubated for 1 hr at 37° C. before adding 50 ml of goat anti-CTB at 10 mg/ml in 5% NGS-PBS. The mixture was then incubated for 1 hr on ice before adding 50 ml of SaC, mixed well, then incubated on ice for another 1 hr with intermittent mixing. The SaC was washed twice with PBS, and SaC-precipitated virus was lysed with 400 ml of 1% Triton X-100 in cRPMI at room temperature for 30 min. Released p24 was measured with a standard p24 ELISA after pelleting the SaC.

Immunomicroscopy

Cell surface staining of chronically infected cells and uninfected cells was performed under saturating conditions. Jurkat cells ($3\times10^5$) were washed in cold PBS and preincubated on ice for 15 min in 5% NGS-PBS. Uninfected cells were incubated with 1 to 5 mg of MAb in 5% NGS-PBS for 30 min on ice, washed with PBS, and incubated with 2 mg of Texas red-conjugated GAM IgG. Infected cells were incubated with biotinylated human anti-HIV polyclonal antibody (10 mg/ml in 5% NGS-PBS) for 30 min on ice and washed with PBS before incubating them with 2 mg of Texas red-streptavidin conjugate. Both cell types were incubated with the second primary MAb at 1 to 5 mg in 5% NGS-PBS 30 min on ice, washed with PBS, and incubated with 2 mg of FITC-GAM in 5% NGS-PBS. The cells were then fixed with 2% paraformaldehyde in PBS and cytospun onto poly-L-lysine-coated slides by using Cyto Funnels (Shandon; Pittsburgh Pa.). The pellets were overlaid with 50 ml of 25% glycerol in PBS, and a coverslip was positioned over the droplet. The edges of the slides were sealed with nail polish before storing them at 4° C. This staining procedure was also performed with cells prefixed with 2% paraformaldehyde in PBS prior to MAb staining. Viewing of slides was per-formed with an Olympus IX50 confocal microscope under oil immersion at an ×100 magnification. Micrographs were analyzed on a Silicon Graphics Work-station with Intervision software. Final images were enhanced on the Silicon Graphics Workstation by two-dimensional deconvolution, and brightness and contrast were adjusted for viewing.

Cell Lysis and Equilibrium Centrifugation

Protein extraction and equilibrium centrifugation were performed as previously described with slight modifications (Ilangumaran et al., Anal. Biochem. 235:49-56, 1996, which is incorporated herein by reference). Briefly, $2\times10^7$ cells were washed twice in PBS and once in TKM buffer (50 mM Tris-HCl, pH 7.4; 25 mM KCl; 5 mM $MgCl_2$; 1 mM EDTA). Cells were extracted on ice for 30 min in 500 ml of lysis buffer (TKM, 1% Triton X-100, 2 mg of aprotinin per ml). Lysates were centrifuged at 8,000×g for 10 min at 4° C., and the supernatants were stored at −20° C. For equilibrium centrifugation, extracts were adjusted to 40% sucrose in TKM and loaded into SW41 tubes. The extracts were overlaid with 6 ml of 38% sucrose-TKM, followed by 4.5 ml of 5% sucrose-TKM. Tubes were centrifuged at 100,000×g for 18 hr at 4° C. Eleven 1 ml fractions were collected from the bottom of the tube and stored at −20° C.

Dot Immunoassay

Dot immunoassays were performed as described previously with minor modifications (Ilangumaran et al., supra, 1996). Briefly, 100 ml portions of each fraction diluted 1:10 in PBS ($2 \times 10^5$ cell equivalents) were added to wells of a Bio-Dot apparatus (Bio-Rad; Hercules Calif.), gently suctioned onto nitrocellulose membranes, and allowed to air dry. The membranes were cut into strips and stored at $-20°$ C. in plastic bags. Before blotting, strips were blocked with 5% nonfat milk powder in TBST (10 mM Tris-HCl, pH 7.5; 100 mM NaCl; 0.1% Tween 20) for 1 hr at room temperature. Strips were then incubated with primary antibodies in TBST/0.5% milk powder for 1 hr, and washed 10 min three times with TBST, followed by incubation with HRP-conjugated GAM for 45 min. The strips were then washed five times and developed with an enhanced chemiluminescence (ECL) assay (Amersham Life Science; Arlington Heights Ill.) before exposure to Hyper-Film ECL.

Dialkylindocarbocyanine Labeling

Three million Jurkat HIV-$1_{RF}$-infected cells were washed with PBS and resuspended in 1 ml of cRPMI. DiIC16 or DiIC12 (1,19-didodecyl-3,3,39,39-tetramethylindocarbocyanine; Molecular Probes; Eugene Oreg.; Arthur et al., supra, 1992) in 0.1 mg of ethanol per ml was added to make a final concentration of 1 to 10 mM. Cells were incubated on ice for 15 min to allow the incorporation of dyes. The cells were washed with PBS and fixed with 2% paraformaldehyde in PBS before further MAb labeling for confocal microscopy.

($^3$H)-Myristic Acid Labeling and Immunoprecipitation

HIV-1-infected Jurkat cells ($2 \times 10^7$) were labeled in 2 ml of cRPMI containing 1 mCi of (9,10(n)-$^3$H)-myristic acid (40 to 60 Ci/mmol; Amersham Pharmacia Biotech.; Piscataway N.J.) for 4 hr at room temperature. Labeled cells were lysed and subjected to sucrose gradient equilibrium centrifugation as described above. GEM domain (lipid raft) fractions 3, 4, and 5 were pooled as were soluble fractions 8, 9, and 10. Samples were pre-cleared by incubation with 20 ml of normal human serum for 1 hr at 4° C. before adding 100 ml of SaC and incubating them an additional 30 min. The preimmune complexes were removed, and samples were incubated with excess IgG1 myeloma or Gag.M1 MAb for 1.5 hr at 4° C., followed by the addition of 2 mg of RAM (Fc specific). After 1 hr, 50 ml of SaC was added, followed by incubation for 30 min. Immune complexes were washed twice with PBS and resuspended in 200 ml of PBS. Samples were then boiled, and the supernatant was blotted onto a nitrocellulose membrane with a Bio-Dot apparatus. The membrane was treated with En$^3$Hance Spray (DuPont; Wilmington Del.), then exposed to Hyperfilm-MP (Amersham) for 5 days. Dots were quantitated by densitometry analysis by MacBAS software version 2.5, and the percent distribution in GEM domains was determined by using the following formula:

$$(Gag_{GEM-IgGGEM})/\{(Gag_{GEM}-IgG_{GEM})+(Gag_{Sol}-IgG_{Sol})\}.$$

Results

Microfluorimetry of infected Jurkat cells showed high expression of CD45 and low expression of Thy-1 and CD59. Flow cytometry under saturating conditions was used to determine the expression of CD45, Thy-1, and CD59 on the surface of infected Jurkat cells. CD45 was highly expressed on Jurkat cells (see Nguyen and Hildreth, J. Virol. 74:3264-3272, 2000, which is incorporated herein by reference; see FIG. 1). An antibody against MHCI was used as a positive control, while mouse myeloma immunoglobulin (IgG1) was used as a negative control. Expression of Thy-1 and CD59 were significantly lower than that of CD45 and MHCI. These results correlate with previous surface expression analyses (Orentas and Hildreth, supra, 1993) and was corroborated by conventional immunofluorescence staining.

HIV-1 incorporated the GPI-linked proteins, Thy-1 and CD59, and ganglioside GM1. The virus phenotyping assay, in which HIV-1 particles are captured by MAbs through host proteins present on the viral particle surface, was used to determine the relative host protein phenotype of HIV-1 particles. The relative p24 captured by the MAbs was determined in three experiments. MAbs to gp41 and MHC I captured virus efficiently. Thy-1 and CD59 also supported efficient viral capture despite low expression on the host cell surface. However, very little HIV-1 was captured through CD45 despite very high expression of CD45 on the cell surface. The failure of the anti-CD45 MAb (H5A5) to capture HIV-1 was not due to low MAb affinity or failure to bind to the capture plate (see Orentas and Hildreth, supra, 1993). The H5A5 MAb also was capable of capturing HRP-labeled Jurkat cells in a similar assay as efficiently as MAbs against other membrane proteins (see Nguyen and Hildreth, supra, 2000; FIG. 1). Thus, the failure of anti-CD45 MAb to capture virus was not due to a failure of the MAb to work in the capture assays.

These results demonstrate a significant preference for HIV-1 incorporation of GPI-linked proteins as compared to CD45. The high expression of CD45 on the cell surface and its low incorporation into virus particles was consistent with exclusion of this molecule from budding particles. To corroborate the MAb plate capture assay results, HIV-1 immunoprecipitations were performed with MAbs. This assay allowed for the potential interaction of all the virions in solution with the MAbs, in contrast to the plate virus capture assay, in which only a small fraction of the particles make contact with the MAbs. The anti-gp41 MAb, T32, which was used as a positive control for intact virions, precipitated up to 60% of the p24 in the supernatant, depending on the virus preparation. The anti-CD59 MAb precipitated as much p24 as anti-gp41 MAb T32. However, even in this assay, anti-CD45 MAb captured very little virus.

The effects of 2-OH-βCD, a cellular cholesterol efflux inducing molecule, on the incorporation of host molecules into virions also was examined. By removing cholesterol, 2-OH-βCD is believed to partially perturb organized lipid rafts, resulting in dispersal of their components (Ilangumaran and Hoessli, Biochem. J. 335:433-440, 1998). The capture of HIV-1 by MAbs against CD59 and gp41 decreased substantially ($P<0.05$) after treating cells with 2-OH-βCD, as measured by the percentage of total p24 (see Nguyen and Hildreth, supra, 2000; FIG. 2). The decrease in Thy-1 was not statistically significant ($P=0.08$). CD45 capture remained mostly unaffected. The effects on virus precipitation through gp41 indicate that intact lipid rafts are required for efficient gp41 incorporation into virions, since the overall cellular release of p24 actually increased after 2-OH-βCD treatment.

The relative incorporation of GM1, a ganglioside marker specific for lipid rafts, also was examined. Using a soluble CTB binding assay, as much as 75% of HIV-1 was precipitated using goat anti-CTB and SaC after treating the virus with GM1-specific CTB (see Nguyen and Hildreth, supra, 2000; FIG. 3). The CTB binding to virus was specific and dose dependent, and no virus was precipitated in the absence of CTB as measured by p24 ELISA. These results demonstrate that the majority of HIV-1 particles incorporated the lipid raft-specific marker GM1.

Thy-1, CD59, and GM1 colocalized with HIV-1 proteins on infected cell uropods, which excluded CD45. To determine the distribution of HIV-1 proteins relative to GPI-linked proteins that serve as lipid raft markers, infected cells were subjected to immunofluorescence staining followed by confocal microscopy. Expression of HIV-1 proteins was localized to uropods projecting from one end of the cell. This capping pattern was seen on most cells in the infected cell culture. Uropods protruding from HIV-1-infected cells have been described for adherent T cells. Thy-1 and CD59 both colocalized with cell surface HIV-1 proteins, as shown by a superimposed green (Thy-1 or CD59) and red (HIV-1 proteins) fluorescence (see Nguyen and Hildreth, supra, 2000; FIG. 4). Cells that were prefixed with 2% paraformaldehyde before staining showed a similar appearance, indicating that the colocalization was not due to antibody crosslinking of viral and GPI-linked proteins. Since the cells were not permeabilized before staining, the HIV proteins seen in these studies are likely gp41 and gp120. This was confirmed in studies with anti-gp41 MAb T32 in the colocalization studies. Uninfected cells showed no capping of Thy-1 or CD59. CD45 did not localize to areas of HIV-1 protein expression and was excluded from uropods. The distribution of CD45 was unaffected by HIV-1 infection, and the molecule remained evenly dispersed in patches all over the cell surface. These results confirm those obtained using the virus phenotyping studies. The ability of GM1 to colocalize on the cell surface with HIV-1 proteins was examined to confirm the finding that GM1 was present on virions. GM1 staining was relatively faint with rabbit anti-GM1 antibody, but confocal microscopy showed colocalization of this molecule with HIV-1 labeled cells.

The lipid raft-partitioning lipid analog, DiIC16, colocalizes with HIV-1 proteins on uropods of infected cells. In order to evaluate the localization of lipids in lipid rafts, two forms of dialkylindocarbocyanine, a fluorescent lipid analog, were used—DiIC16, which partitions preferentially to lipid-ordered domains due to its two 16-carbon saturated fatty acid chains, and DiIC12, which, with its two 12-carbon saturated fatty acid chains, partitions to fluid domains. Infected Jurkat cells were labeled with the dyes for 15 min on ice, washed with PBS, and fixed with 2% paraformaldehyde in PBS. Cells were then stained with soluble CD4Ig or human anti-HIV polyclonal antibody and FITC-labeled sheep anti-human IgG to detect surface gp120/41.

Confocal microscopy showed that cells labeled with DiIC16 extensively colocalized with HIV-1 proteins (see Nguyen and Hildreth, supra, 2000; see FIG. 5). In contrast, DiIC12 did not preferentially label uropods and was specifically excluded from areas with HIV-1 staining. As expected, CD45 staining was also excluded from uropods that stained positive for DiIC16 and HIV-1.

HIV-1 proteins were detected in isolated lipid raft fractions. Lipid rafts were purified by cell lysis and equilibrium centrifugation in order to confirm the presence of HIV-1 proteins in these membrane structures. The fractions were assayed for the presence of viral and host proteins by immunoblot analysis. The separation of detergent-resistant lipid rafts was confirmed by the abundance of Thy-1 and CD59 in fractions 3 through 5, while CD45 was present only in the bottom fractions 9 and 10 (see Nguyen and Hildreth, supra, 2000; FIG. 6). Immunoblot detection of membrane fractions revealed that the HIV MA protein, p17, and gp41 were both present in the detergent-insoluble lipid rafts of infected cells. The distribution between GEM domains and soluble fractions was quantitated by MacBAS software version 2.5. Since lysates were prepared from whole cells, the anti-MA MAb could bind not only the membrane associated MA protein, but also non-membrane-associated forms of the group-specific antigen precursor protein (Gag) and MA, thus accounting for the abundance of p17 detected in the soluble fractions of the blot.

A possible mechanism for the targeting of the HIV Env protein, gp41, to lipid rafts involves palmitylation of two cysteines in its cytoplasmic tail (see Yang et al., *Proc. Natl. Acad. Sci., USA* 92:9871-9875, 1995). Dual acylation of host proteins involving palmitate and myristate target proteins to lipid rafts (Robbins et al., supra, 1995). As expected, a substantial portion of the transmembrane subunit of Env, gp41, also was present in the GEM fractions. Theses results indicate that palmitylated gp41 partitions specifically to lipid rafts. Since palmitylation is a reversible post-translational modification, it is not likely that all of the gp41 present in the cell is palmitylated at any given time. This could account for the large proportion present in soluble domains. Other transmembrane proteins, such as MHC I and CD63, previously shown to be incorporated into HIV-1, were detected in lipid rafts as well, although the majority of both molecules are in the solubilized fractions Myristylated HIV-1 Gag partitioned to GEM domains. The myristylation of Gag is necessary for membrane association, proteolytic processing, and virus budding. As such, it may be expected that, with a mixed population of myristylated and non-myristylated Gag within a cell, only the myristylated forms will be responsible for membrane association and potentially determining the site of virus budding. To ensure that cellular Gag and not virus-associated Gag was being examined, a MAb specific for p24 and p55 was used. To determine which areas of the membrane myristylated Gag would bind, cells were labeled with ($^3$H)-myristic acid and isolated lipid rafts were examined. Lipid raft fractions and soluble fractions were pooled separately and immunoprecipitated with an anti-Gag MAb. Blotting of the precipitated proteins showed that myristylated Gag protein was present predominantly in the lipid raft fractions (see Nguyen and Hildreth, supra, 2000; FIG. 7). The blots were quantitated by densitometry, and the IgG backgrounds were subtracted from each to determine the distribution of the myristic acid label expressed as a percentage of the total. More than 90% of the cellular myristylated Gag was in lipid rafts. This result is consistent with the observation that myristylation targets a number of host proteins, such as Src, Lck, Lyn, and HCK protein tyrosine kinases, to lipid rafts as well.

In summary, these results demonstrate that HIV-1 budding occurs through lipid rafts, thus accounting for the cholesterol-rich, sphingolipid-rich virus membrane, which bears GPI-linked proteins such as Thy-1 and CD59, and for the lack of CD45, which is not associated with lipid rafts in cells.

EXAMPLE 2

Host Membrane Cholesterol is Required For HIV-1 Infection

This example demonstrates that intact lipid rafts and cholesterol are required for HIV-1 infection and syncytium formation.

Cells and Reagents

Jurkat, PM 1, and CEM×174 cell lines were obtained from the American Type Culture Collection (Rockville Md.) and maintained in cRPMI as described in Example 1. Peripheral blood mononuclear cells were isolated from leukopheresis buffy coats and stimulated with PHA as previously described (Gomez and Hildreth, supra, 1995). Control mouse myeloma IgG1 and rabbit anti-mouse IgG (Fc specific) were purchased from Jackson Immunoresearch (West Grove Pa.). MAbs to MHC class I antigen (MHM.5), MHC class II antigen (MHM.33), CD4 (SIM.4), CXCR4 (FSN.NT.M3) and CD45 (H5A5) were produced as described in Example 1.

2-OH-βCD Treatment and Virus Production

PM1 cells chronically infected with HIV-$1_{RF}$ were washed and treated with 20 mM 2-OH-βCD in cRPMI or with cRPMI alone for 1 hr at 37° C. The cells were then washed twice before resuspension at a density of $5\times10^6$/ml in cRPMI. The cells were incubated for 6 hrs at 37° C., 5% $CO_2$ and pelleted by centrifugation. Supernatants, which contained the virus, were collected and purified by centrifugation through a 20% sucrose cushion (Liao et al., supra, 2000). The virus pellets were taken up in cRPMI and titrated against LuSIV cells to determine infectivity. P24 was measured in a standard p24 ELISA.

Cholesterol Measurement

Cellular cholesterol was measured with a sensitive cholesterol oxidase-based fluorimetric assay (Amplex Red Cholesterol Kit) from Molecular Probes (Eugene Oreg.). Cholesterol content of cells was normalized to total cellular protein.

Syncytium Assays

Syncytium assays were carried out essentially as previously described (Hildreth and Orentas, supra, 1989). Briefly, cell lines or PHA blasts were treated with 20 mM 2-OH-βCD in RPMI 1640 or medium alone for 1 hr at 37° C. before washing twice with PBS. The treated cells were then mixed with HIV-1 infected cells, each at density of $2\times10^6$/ml, in cRPMI and incubated at 37° C. Syncytia were scored and photographed 3 to 6 hr after mixing. For free-virus mediated syncytium assays ("fusion from without"), HIV-$1_{RF}$ from infected PM1 culture supernatants were clarified by 0.45 Tm filtration (p24 concentration greater than 500 ng/ml). 2-OH-βCD-treated and non-treated cell lines were added to the virus preparations and incubated at 37° C. for 3 hr before counting syncytia.

Flow Cytometry

Flow cytometry was performed as previously described (Orentas and Hildreth, supra, 1993). Briefly, $2\times10^5$ 2-OH-βCD treated or untreated cells in 100 μl PBS containing 5% normal goat serum (NGS) were added to 100 μl of MAb (1-5 μg) and incubated 30 min on ice. In comparative experiments we prefixed the cells with 2% paraformaldehyde in PBS immediately after 2-OH-βCD treatment. Cells were washed with PBS, resuspended in 100 μl of PBS, 5% NGS containing 2 Tg of FITC conjugated-goat anti-mouse IgG (FITC-GAM) and incubated 1 h on ice. Cells were then washed with PBS and fixed with 2% paraformaldehyde followed by analysis on an EPICS Profile II flow cytometer.

Confocal Microscopy

Cell-surface staining of 2-OH-βCD-treated and untreated cells was performed under saturating conditions. 2-OH-βCD-treated and untreated PHA blasts ($3\times10^5$) were washed in cold PBS and pre-incubated on ice for 15 min in 5% NGS/PBS. Cells were then incubated with MAb 1-5 μg in 5% NGS/PBS 45 min on ice, washed with PBS and then incubated with 2 μg of FITC-GAM in 5% NGS/PBS. The cells were then fixed with 2% paraformaldehyde in PBS and spun onto poly-L-lysine coated slides using cyto-funnels. The pellets were overlaid with 50 μl of 25% glycerol in PBS and a coverslip was positioned over the droplet. The edges of the slides were sealed with nail polish before storing them at 4° C. This staining procedure was also performed with cells pre-fixed with 2% paraformaldehyde in PBS prior to MAb staining. Viewing of slides was performed with an Olympus IX50 confocal microscope under oil immersion at 100x magnification. Micrographs were acquired onto a Silicon Graphics Workstation with Intervision software. Final images were enhanced on the Silicon Graphics Workstation by two-dimensional deconvolution, and brightness and contrast were adjusted for viewing.

Free Virus Binding Assay

Virus binding was measured through host cell antigen transfer as described (Liao et al., supra, 2000). Briefly, Jurkat cells ($1\times10^6$) were washed with serum free RPMI-1640 medium (iRPMI) before incubation in 20 mM 2-OH-βCD in iRPMI or iRPMI alone for 1 hr at 37° C. Cells were then washed twice with iRPMI before adding 100 Tl of clarified HIV-1 supernatant (>10 ng/ml of p24 from PM1 cells) for 1 hr on ice. Excess virus was removed by washing twice with iRPMI. MAbs were then added at 20 ug/ml in 5% NGS/PBS and allowed to incubate for 1 h on ice before washing with iRPMI. FITC-GAM (10 ug/ml) was then added for 45 min on ice before washing with iRPMI. Cells were then fixed with 2% paraformaldehyde followed by analysis on an EPICS Profile II flow cytometer.

Primary Virus Infection Assay

Peripheral blood mononuclear cells (PBMCS) were isolated by Ficoll-Hypaque centrifugation from buffy coats obtained from the Johns Hopkins Hemapheresis Center. Cells were stimulated for 3 days with 3 Tg/ml PHA, washed with iRPMI, and treated with 10 mM 2-OH-βCD in cRPMI for 1 hr. Cells were then washed twice with iRPMI and resuspended in cRPMI ($1\times10^6$/ml) supplemented with 50 U/ml IL-2 and containing primary HIV-1 strains at 20 ng/ml p24. Cells were incubated with virus for 24 hr at 37° C. before washing twice with iRPMI. Cells were then resuspended in cRPMI supplemented with 50 U/ml IL-2 and cultured for 6 days at 37° C. Supernatants were collected and p24 was quantitated by standard p24 ELISA.

Luciferase-based Infectivity Assay

The effect of 2-OH-βCD on infectivity of HIV was measured in a Luciferase-based single cycle infection assay as previously described (Liao et al., supra, 2000). LuSIV cells were treated with 20 mM 2-OH-βCD in iRPMI or iRPMI alone for 1 hr at 37° C. Cells were then washed with iRPMI before being resuspended in cRPMI at a density of $2\times10^6$/ml. Cells in 100 Tl were mixed with cRPMI or with dilutions of virus supernatant (62 to 500 pg/ml of p24) from 2-OH-βCD-treated or untreated PM1 cells and allowed to incubate overnight (16 hr) at 37° C. The LuSIV cells were washed with PBS and lysed with 100 Tl of Reporter Lysis Buffer (Promega). After centrifugation at 13,000×g for 30 seconds, 10, μl of lysate were added to 100 μl Luciferase Reagent (Promega) in an opaque 96 well plate and luminescence was measured on a Packard Lumicount luminometer (Downers Grove, Ill.).

SDF-1α-Induced Cell Adhesion Assay

Cell adhesion assays were carried out essentially as previously described (Liao et al., supra, 2000). The wells of 96 well plates were coated with recombinant ICAM-Ig and blocked as described. Jurkat cells were labeled with horseradish peroxidase (HRP) and treated with either 20 mM 2-OH-βCD or medium alone as described above. The cells were then washed and resuspended in cRPMI at a density of $2\times10^6$/ml. One hundred Tl of cells were added to the wells along with cRPMI alone or medium containing 10 ng/ml of SDF-1α. The wells were incubated at 37° C. for various times before washing to remove unbound cells. Bound cells were lysed and HRP measured as described previously. A standard curve was generated by from known numbers of labeled cells lysed and quantitated by measuring HRP.

Results

2-OH-βCD treatment blocked syncytium formation of primary cells and cell lines. The role of lipid rafts in the HIV-1 fusion process was examined by treating CD4+HIV-susceptible target cells with 2-OH-βCD to deplete membrane cholesterol and disperse lipid rafts. Treatment of cells with 10 to 20 mM 2-OH-βCD for 1 hr at 37° C., followed by washing to remove free 2-OH-βCD, depleted greater than 70% of total cellular cholesterol without any loss in cell viability as measured by Trypan Blue exclusion. Furthermore, treated cells continued to grow normally after 2-OH-βCD treatment when placed back into culture in cholesterol-containing medium. The non-toxicity of βCD treatment was further demonstrated by finding 2-OH-βCD treated Jurkat cells still showed $Ca^{2+}$ flux responses to anti-CD3 MAb.

CD4+SupT1 T cells formed numerous large syncytia within 3 hr after the addition of HIV-$1_{MN}$-infected H9 cells. 2-OH-βCD treatment of SupT1 cells completely inhibited syncytium formation with HIV-$1_{MN}$-infected H9 cells. No syncytia were apparent in this culture for more than 15 hr, which can reflect the recovery time for cholesterol in the βCD treated T cells. 2-OH-βCD was washed out after the 1 hr treatment and was not present during the co-cultivation step. As such, the effects are not a result of a steric blockade by 2-OH-βCD, which can bind to cells.

To confirm that the effects of the βCD on syncytium formation were due to cholesterol depletion, cells were treated with 2-OH-βCD that had been pre-loaded (saturated) with cholesterol (CH-βCD) and, therefore, was unable to deplete cellular cholesterol. Cells treated with the CH-βCD fused to HIV-1-infected cells as efficiently as control untreated cells, thus confirming that the βCD blocked HIV-induced fusion by depleting cholesterol. Similar results were obtained when primary cells (PHA stimulated T cells) that had been treated with 2-OH-βCD or CH-βCD were used as fusion partners with HIV-infected cells.

The effect of βCD treatment on HIV-induced fusion of several other cell lines also was examined. Four CD4+, CXCR4+cell lines, SupT1, H9, PM1, and MT2, were treated with 2-OH-βCD and tested for syncytium formation with HIV-1-infected cells. In each case, syncytium formation was completely blocked by depleting cellular cholesterol (see Table 1). These results demonstrate that cholesterol and intact lipid rafts are required for HIV-induced syncytium formation.

TABLE 1

2-OH-βCD Effects on CD4 and CXCR4 Surface Expression and Syncytium Formation of Cell Lines with HIV-infected H9 Cells

| Cell Line | Syncytia (/HPF) | | CD4 (MCF) | | CXCR4 (MCF) | |
|---|---|---|---|---|---|---|
| | Control | βCD | Control | βCD | Control | βCD |
| MT2 | 55 ± 10 | 0 | 65.3 | 62.2 | 30.1 | 16.7 |
| PM1 | 71 ± 5 | 0 | 78.6 | 85.9 | 16.2 | 3.1 |
| H9 | 52 ± 3 | 0 | 21.2 | 20.9 | 29.9 | 6.7 |
| SupT1 | 63 ± 8 | 0 | 140.1 | 188.3 | 44.9 | 15.0 |

"MCF" indicates mean channel fluorescence.
"βCD" indicates treatment with 20 mM 2-OH-βCD in medium.

The effect of cholesterol depletion on virus-cell fusion ("fusion from without") was also determined. CD4+/CXCR4+cell lines (MT2, SupT1, PM1) incubated with free HIV-$1_{RF}$ at concentrations greater than 500 ng/ml of p24 for 3 hr at 37° C. showed extensive syncytium formation (>30 syncytia per HPF), whereas cells treated with 2-OH-βCD showed no syncytium formation when exposed to virus under the same conditions. Although low levels of fusion that do not proceed to gross syncytia cannot be detected, these results indicate that cholesterol depletion blocked HIV-induced cell-cell fusion from without, which first requires extensive virus-cell fusion to put HIV envelope proteins into cell membranes. These results indicate that cholesterol depletion prevents fusion of HIV particles to cells.

Cholesterol depletion also promoted CXCR4 down-modulation by MAb-induced internalization. A possible explanation for the inhibition of syncytium formation by cholesterol depletion as described above is that CD4, CRs, or both are lost from the cell surface, for example, by extrusion from the membrane in vesicles after loss of cholesterol, or they could be internalized. To explore these possibilities, βCD treated cells were examined for expression of HIV receptors by flow cytometry. CD4 expression did not change after treatment with 2-OH-βCD in PHA blasts or any of the cell lines tested (Table 1). In contrast, cell surface expression of CXCR4 was reduced by 50% or more in all of the cells after 2-OH-βCD treatment (Table 1). PM1 cells showed the most significant loss of CXCR4 expression, with a drop in total mean channel fluorescence (MCF) from 16.2 to 3.1. Primary T cells showed a similar reduction in CCR5 expression, from 19% to 8% of cells staining positive.

In order to determine whether the loss of CXCR4 expression was due to MAb-induced internalization, cells were fixed with 2% paraformaldehyde in PBS immediately after 2-OH-βCD treatment and before staining with MAbs for flow cytometry. Under these conditions both CD4 and CXCR4 expression remained unchanged on the cell surface (Table 2). 2-OH-βCD-treated cells fixed and permeabilized after the MAb binding step showed no significant reduction in anti-CXCR4 MAb staining compared to control cells. These results demonstrate that CXCR4 remains on the surface after βCD treatment, but is rapidly internalized following MAb binding.

TABLE 2

2-OH-βCD Treatment Does Not Down modulate CXCR4

| | CD4 (MCF) | | CXCR4 (MCF) | |
|---|---|---|---|---|
| Cell line | Control | βCD | Control | βCD |
| PM1 | 146 | 129 | 63 | 64 |
| H9 | 46 | 50 | 45 | 55 |
| SupT1 | 216 | 213 | 94 | 91 |

Cells were fixed with 2% paraformaldehyde in PBS immediately after βCD treatment before performing flow cytometry.
"MCF" indicates channel fluorescence; 2-OH-βCD treatment (20 mM).

Immunostaining and confocal microscopy of βCD-treated PHA blasts and control cells showed that CXCR4 was not significantly redistributed on the cell surface after cholesterol depletion. Patchy staining of CXCR4 persisted after 2-OH-βCD treatment whether the cells were fixed before or after mAb staining. Consistent with flow cytometry data, overall staining was reduced in the βCD-treated cells that were not fixed before the MAb staining procedure. The distribution of CD4 and CD45 was unchanged on the cell surface after 2-OH-βCD treatment. These results demonstrate that the overall membrane expression and distribution of critical HIV receptors were essentially unchanged after βCD treatment and suggest that the cholesterol content of the cell membrane is a critical factor in HIV-induced membrane fusion.

βCD treatment reduced HIV-1 binding. The possibility that βCD treatment affected virus binding or interactions between gp120 and CD4 or CRs was examined. In order to measure virus binding to cells, a flow cytometry assay was used that measures the transfer of host cell class II MHC proteins to class II MHC-negative cells by HIV virions, which incorporate large numbers of these proteins into their lipid envelopes. This approach previously was used to demonstrate adhesion molecule-mediated binding of HIV to cells (Liao et al., supra, 2000). Class II MHC-negative Jurkat cells were used as target cells in the HIV binding assay. As a positive control for flow cytometry analysis, class I MHC molecules were probed on the Jurkat cells, which were stained equally well with MAb against this protein before and after 2-OH-βCD treatment (Table 3). When HIV-1$_{RF}$ from class II MHC-positive PM1 cells was added to untreated Jurkat cells, class II MHC MAb mean channel fluorescence increased from 1.0 to 7.8 relative fluorescence units, while the percentage of positive cells increased from 3.0% to 55.4% (Table 3). 2-OH-βCD treatment of the cells reduced virus binding by 70%, as determined by mean channel fluorescence of the anti-class II MHC mAb. These results demonstrate that HIV-1 remains capable of measurable attachment after cholesterol depletion of target cells, but at much lower levels.

βCD treatment blocks HIV-1 virus infection. HIV-1 can spread in cell cultures without necessarily exerting cytopathic effects. Thus, inhibition of syncytium formation by cholesterol depletion and lipid raft dispersion does not necessarily mean that HIV infection by free virus also is blocked. To test the effects of cholesterol depletion on HIV-1 infection of primary T cells by free virus, PHA blasts were treated with 10 mM 2-OH-βCD or medium alone, then were exposed to HIV-1 for 2 hr before washing to remove input virus. Viability and growth of the PHA blasts was not affected by treatment with the βCD under the conditions used. P24 release was measured after an addition 6 days in culture. Two primary strains of HIV-1, 97.099 and 97.534, M-tropic (R5) and dual-tropic (X4R5), respectively, were tested. The results were identical to those obtained in syncytium formation assays; 2-OH-βCD treatment of PHA blasts completely inhibited infection by HIV isolate 97.099, while infection by isolate 97.534 was inhibited by more than 70%.

The effects of βCD treatment on HIV infectivity were measured in a sensitive single-cycle infection assay based on a cell line transfected with an LTR-luciferase cassette. The CD4+CEM×174 (LuSIV) cells possess a modified SIV LTR viral promoter linked to the luciferase gene. Quantitative measurements of single round infection are obtained with this

TABLE 3

2-OH-βCD Reduces Binding of HIV-1 to Target Cells

| | IgG1 MCF (% Pos) | | MHM5 MCF (% Pos) | | MHM33 MCF (% Pos) | |
|---|---|---|---|---|---|---|
| | Control | βCD | Control | βCD | Control | βCD |
| No virus | 0.9 (2.4) | 0.7 (3.4) | 158.6 (100) | 165 (100) | 1.0 (3.0) | 0.7 (3.3) |
| HIV$_{RF}$ | ND | ND | 164 (99.9) | 167.8 (100) | 7.8 (55.4) | 2.4 (26.0) |

HIV binding to Jurkat cells (control and 2-OH-βCD-treated) was measured by transfer of class II MHC molecules. MAbs used were MHM.5 (anti-class I MHC), positive control; MHM.33 (anti-class II MHC). "MCF" indicates mean channel fluorescence. "% Pos" indicates percent positive cells. "ND" indicates not determined.

2-OH-βCD treatment blocked CR-induced LFA-1 function. The results described above suggested that intact lipid rafts were required for stable membrane expression of CXCR4. Loss of CXCR function in regulating LFA-1 could also explain the lower binding of HIV-1 to βCD-treated cells observed previously (Liao et al., supra, 2000; Orentas and Hildreth, supra, 1993). As before, the treatment with βCD had no effect on cell viability. The ability of βCD treatment of cells to affect control of LFA-1 function by CXCR4 also was examined. Jurkat cells were treated with 2-OH-βCD or medium alone, then were added to the wells of culture plates coated with soluble recombinant ICAM-Ig. SDF-1, a CXCR4-specific chemokine that triggers LFA-1 function, was added to trigger binding of LFA-1 to ICAM-1. Control cells responded to SDF-1 and, as expected, bound very well to ICAM-Ig. In contrast, the βCD-treated Jurkat cells showed no binding to ICAM-Ig after exposure to SDF-1. These results are consistent with previous reports showing disruption of integrin function by cholesterol depletion. CXCR4-specific gp120 triggers the same responses through CXCR4 as SDF-1 (Iyengar et al., *J. Immunol.* 162:6263-6267, 1999). These results indicate that HIV-1 particles cannot trigger LFA-1 function on βCD-treated cells, which may explain lower virus binding to such cells.

assay system (Roos et al., *Virology* 273:307-315, 2000, which is incorporated herein by reference). Viability of LuSIV cells as determined by trypan blue exclusion and proliferation was not affected by 2-OH-βCD treatment. βCD treatment of LuSIV cells reduced HIV infection by almost 100%, and the effects were readily seen at all viral input levels. The effect of the βCD treatment of LuSIV cells on HIV infection was completely reversed by exposing the 2-OH-βCD-treated cells to CH—BCD (48 Tg/ml cholesterol) for 1 hr to restore membrane cholesterol before exposing the cells to HIV. These results demonstrate that cholesterol in the membrane of HIV susceptible cells is required for infection by free virus.

EXAMPLE 3

β-Cyclodextrin Blocks Vaginal Transmission of Cell-Associated HIV-1

These results demonstrate that topical administration of a βCD reduces transmission of cell-associated HIV-1 through vaginal epithelium.

Cell Culture

Blood was obtained from HIV-negative volunteers by the Johns Hopkins University Hemapheresis Laboratory. HuPBMC were isolated using Ficoll-Hypaque (Pharmacia; Uppsala, Sweden) and were washed and suspended at $5 \times 10^7$/ml in PBS prior to intraperitoneal administration to SCID mice. HuPBMC that were used as inocula were maintained in cRPMI (RPMI-1640 supplemented with 10% FCS, penicillin, streptomycin and gentamycin. PBMC were stimulated with PHA (Sigma) for 2 days; cells were exposed to 300 $TCID_{50}$ (50% tissue culture infective dose) of $HIV-1_{Ba-L}$ in cRPMI with IL-2 (10 U/ml, Boehringer Mannheim). Infected-cell cultures were maintained in cRPMI with IL-2 for 10 days prior to inoculation into the mice.

Limiting dilution-PCR was performed using HIV-1 gag-specific primers as described previously (Markham et al., Proc. Natl. Acad. Sci., USA 95:12568-12573, 1998, which is incorporated herein by reference) to determine the extent to which HuPBMC were infected with HIV-1. To asses virus recovery from cells harvested from the peritoneal cavities of challenged mice, uninfected HuPBMC were PHA-stimulated and maintained in IL-2-supplemented media ($1\times10^6$/mouse) in preparation for co-culture with peritoneal cells recovered from the HuPBL-SCID mice.

HIV-1 Virus Preparation

A single lot of the inoculum virus, $HIV-1_{Ba-L}$, was purchased (ABI, Inc.; Columbia Md.), aliquoted and stored in liquid $N_2$ until used to infect HuPBMC. The $TCID_{50}$ inoculated was confirmed using MAGI cells (CD4, CCR5, and HIV-LTR-βgal-transfected HeLa), and by titration on peripheral blood-derived monocytes.

Vaginal Infection of HuPBL-SCID Mice with HIV-1

Female mice with severe combined immunodeficiency (C.B-17scid; Bosma et al., Nature 301:527-530, 1983; Bosma and Carroll, Ann. Rev. Immunol. 9:323-350, 1991, each of which is incorporated herein by reference), were obtained from Charles River Laboratories (Wilmington Mass.) or from a SCID mouse colony established using C.B-17 mice from Jackson Laboratories (Bar Harbor Me.).

The mice were treated subcutaneously with 2.5 mg progestin (Depo-Provera® progestin; Upjohn Pharmaceuticals; Kalamazoo Mich.), on the same day as administration of $5\times10^7$ unstimulated HuPBMC intraperitoneally in 1 ml PBS. Seven days following progestin treatment and reconstitution of the SCID mice with HuPBMC, the mice were anesthetized and administered pelleted, cell-free $HIV-1_{Ba-L}$ (up to 106 $TCID_{50}$), supernatant fluids from $HIV-1_{Ba-L}$-infected HuPBL, $HIV-1_{Ba-L}$-infected HuPBL, or $HIV-1_{MN}$-infected HuPBL ($1\times10^6$/mouse). In the βCD experiments, the mice received 2-OH-βCD (3% w/v in PBS) 5 min prior to receiving $1\times10^6$ $HIV-1_{Ba-L}$-infected HuPBL, $1\times10^6$ $HIV-1_{Ba-L}$-infected HuPBL pre-incubated with 3% 2-OH-βCD, or $1\times10^6$ $HIV-1_{Ba-L}$-infected HuPBL suspended in PBS.

Mice remained anesthetized for 5 minutes following intravaginal inoculation by pipette. Extreme care was taken to avoid causing trauma to vaginal tissues. Two weeks later the mice were euthanized and peritoneal cells were recovered by lavage with cold PBS. The cells recovered by lavage (of both murine and human origin) were assayed by DNA-PCR for human β-globin to determine the presence of human cells from the peritoneum and for HIV-1 infection by co-culture with PHA-stimulated HuPBMC.

Vaginal Epithelial Morphology

Four BALB/c and four HuPBL-SCID mice were sham-treated or treated with 2.5 mg Depo-Provera progestin one week prior to the experiment. Mice were euthanized by cervical dislocation and reproductive tissues were collected and dissected. Excised vaginal tissue was fixed (Omnifix; Zymed Laboratories; San Francisco Calif.) overnight and embedded in paraffin, sectioned and stained with hematoxylin and eosin.

Fluorescent In Situ Hybridization (FISH)

Six SCID mice were treated with 2.5 mg progestin, with or without HuPBL reconstitution (i.e., peritoneal transplant of human cells). Spleen with peritoneal mesentery, and vaginal tissues were fixed in paraformaldehyde, and embedded in paraffin. Sections were mounted on slides, de-paraffinized, and made permeable by immersion in 50% glycerol in 0.1X SSC at 90° C., followed by incubation in protease solution (Hyytinen et al., Cytometry 16:93-99, 1994, which is incorporated herein by reference). Sections were then co-denatured with a biotin-labeled, human pan-centromere probe (Cytocell; Oxfordshire, UK) at 75° C., and hybridized overnight. Slides were washed, and bound probe was detected with CY3-conjugated streptavidin (Cytocell). Tissue sections were DAPI counterstained, and examined with epifluorescence microscopy.

Migration of Vaginally-Inoculated Human PBMC

HuPBMC were labeled with bisbenzamide (3 Tg/ml, Sigma); the fluorescent human cells ($1\times10^7$) were added vaginally to Depo-Provera® progestin-treated mice (7 SCID mice and 6 BALB/c), and 4 hr later the iliac lymph nodes of each mouse were removed and homogenized on a cell strainer. Fluorescent (and non-fluorescent) cells were counted by fluorescence and phase-contrast microscopy.

Vaginal Epithelial Toxicity

CF-1 mice were pretreated with 2.5 mg progestin; one week later, three groups of three mice each were inoculated with 50 Tl of either PBS, 1% (w/v) nonoxynol-9, or 3% (w/v) 2-OH-βCD (20 mM). Each test solution also contained the membrane-impermeant DNA binding fluorescent dye, ethidium bromide homodimer-1 (20 TM, Molecular Probes; Eugene Oreg.; Hyytinen et al., supra, 1994). Fifteen min following exposure to the test agents the mice were euthanized, the vaginas were dissected and opened longitudinally, and viewed using a fluorescent microscope and TRITC filter set.

Effect of Progesterone Treatment on Murine Vaginal Mucosa

Studies in non-human primate models of simian immunodeficiency virus (SIV) or chimeric simian-human immunodeficiency virus (SHIV) transmission have frequently pretreated the challenged animals with progesterone, with the stated purpose of synchronizing the estrous cycle among experimental animals. However, this treatment also thins the vaginal epithelium, facilitating viral transmission by this route (see, for example, Sodora et al., AIDS Res. Hum. Retrovir. 14(Suppl.1):S119-123, 1998). Progestin treatment of HuPBL-SCID mice similarly caused the multi-layer, stratified, squamous epithelium of the untreated mouse vagina to assume a cervix-like, single layer, columnar morphology. Thus progestin treatment had the effect of rendering the mouse vagina morphologically unlike the human vagina, and more similar to the human, columnar cervical epithelium, which in organ culture is more readily infected with HIV-1 than is vaginal tissue (Howell et al., J. Virol. 71:3498-3506, 1997). In a series of pilot studies, neither cell-free nor cell-associated HIV-1 could be transmitted in HuPBL-SCID mice by the vaginal route without prior administration of progestin (medroxyprogesterone acetate, Depo-Provera® progestin).

HuPBL-SCID Mice Susceptible to Vaginal Transmission of Cell-Associated HIV-1 but not to Cell-Free HIV-1

To determine whether HuPBL-SCID mice were susceptible to cell-associated or cell-free virus, mice were exposed vaginally to cell-free $HIV-1_{Ba-L}$ (CCR-5-utilizing strain) and $HIV-1_{Ba-L}$ infected human peripheral blood mononuclear cells (HuPBMC; see Table 4.

TABLE 4

Vaginal Transmission of Cell-Associated HIV-1 in HuPBL-SCID mice[a]

| HIV inoculum | Number of mice from which HIV-1 was cultured/ Number of mice exposed to HIV-1 |
|---|---|
| HIV-1$_{Ba-L}$-infected HuPBMC | |
| 1.00 × 10$^6$ cells | 5/5* |
| 0.25 × 10$^6$ cells | 4/5* |
| 0.05 × 10$^6$ cells | 1/5 |
| HIV-1$_{Ba-L}$ cell-free virus | |
| 1.0 × 10$^6$ TCID$_{50}$ | 0/5 |
| 1.0 × 10$^5$ TCID$_{50}$ | 0/5 |

*P = 0.048 compared with cell-free virus.
[a]Representative of at least 3 separate experiments of ≧5 mice per group.

High-titer, cell-free HIV-1 and virus obtained from supernatant fluid from the HIV-1 infected HuPBMC used in the same experiment (i.e., recently-budded virus) also were tested. HIV-1 infected HuPBMC were prepared for inoculation into the mice 10 days after in vitro exposure of PHA- and IL-2-stimulated cells to HIV-1. Despite intravaginal inoculation of up to 1×10$^6$ TCID$_{50}$ of cell-free HIV-1$_{Ba-L}$, virus was not transmitted to the HuPBMC that were transplanted intraperitoneally in the mice. However, cell-associated HIV-1$_{Ba-L}$ was efficiently transmitted vaginally in the HuPBL-SCID mice with as few as 250,000 HuPBMC, between 1% and 5% of which were infected with HIV-1 (i.e. as few as 10$^{3.5}$ HIV-1-infected cells). HuPBMC infected to similar levels with HIV$_{MN}$, a CXCR4-using variant, and inoculated intravaginally, transmitted infection much less efficiently (Table 5).

TABLE 5

Vaginal Transmission of Cell-Associated R5-utilizing HIV-1[a]

| HIV inoculum | Number of mice from which HIV-1 was cultured/ Number of mice exposed to HIV-1 |
|---|---|
| HIV-1$_{Ba-L}$(R5)-infected HuPBMC | |
| 1.00 × 10$^6$ cells | 5/5* |
| 0.25 × 10$^6$ cells | 4/5* |
| 0.05 × 10$^6$ cells | 1/5 |
| HIV-1$_{MN}$(X4)-infected HuPBMC | |
| 1.00 × 10$^6$ cells | 1/5 |
| 0.25 × 10$^6$ cells | 0/5 |
| 0.05 × 10$^6$ cells | 0/5 |

*P = 0.048 compared to an equal number of HIV-1$_{MN}$-infected HuPBL.
[a]Representative of at least 2 separate experiments with ≧5 mice per group.

Human PBMC Transplanted into the Peritoneal Cavity of HuPBL-SCID Mice Do Not Populate the Reproductive Tract To determine if human cells placed into the peritoneal cavity could migrate to sites in the vaginal mucosa and/or submucosa, HuPBMC were transplanted into the peritoneal cavities of progesterone-treated, female HuPBL-SCID mice. Seven days later the mice were euthanized and tissue sections of the vagina, spleen and peritoneal mesentery were hybridized with a human pan-centromere probe to detect human cells. Whereas abundant human cells were found in the peritoneal mesentery, and occasionally in the spleen of all the HuPBL-SCID mice, no human cells were detected in the vaginal tissues. Thus, there do not appear to be any locally accessible target cells in the vagina, which free virus can infect following intravaginal inoculation, in these mice.

Vaginally Introduced Human PBMC Migrate to Regional Lymph Nodes of HuPBL-SCID Mice To define the basis for transmission of cell-associated virus, infected and uninfected HuPBMC were examined for the ability to migrate from the vagina to the site of transplanted human cells in the peritoneal cavity. HuPBMC were labeled with bisbenzamide (3 Tg/ml), then the fluorescent human cells (1×10$^7$) were added vaginally to Depo-Provera® progestin-treated mice. Four hr later, the iliac lymph nodes of each mouse were removed and homogenized on a cell strainer. Fluorescent cells were detected in the lymph nodes (mean cell number 204, ranging from 0-395, up to 5% of the cells recovered from the lymph nodes of SCID mice). The human cells migrated to the iliac lymph nodes of both progestin-treated BALB/c and progestin-treated HuPBL-SCID mice.

2-OH-βCD Prevents Cell-Associated HIV-1 Transmission and is Non-Toxic to the Vaginal Epithelium The ability of a βCD to inhibit vaginal transmission of cell-associated HIV-1 was examined. Reconstituted HuPBL-SCID mice were challenged intravaginally with 1×10$^6$ PBMC infected with HIV$_{Ba-L}$ after receiving progesterone subcutaneously and HuPBMC intraperitoneally. For two of the experimental groups the HIV-1 infected PBMC were pre-incubated in either 20 Tl PBS or 2-OH-βCD (3% w/v) before the mixture was inoculated intravaginally. A third group of mice received 20 Tl 2-OH-βCD (3% w/v) intravaginally, followed 5 min later by the infected PBMC in PBS (10 Tl). βCD significantly inhibited cell-associated HIV-1 transmission by this route, even when administered prior to exposure to HIV-1 infected PBMC (Table 6).

TABLE 6

2-OH-βCD Inhibits Vaginal Transmission of Cell-Associated HIV-1

| Treatment of HIV-infected cells | Number of mice from which HIV-1 was cultured/ Number of mice exposed to HIV-1 |
|---|---|
| PBS premixed with HuPBMC | 12/17 |
| 2-OH-βCD premixed with HuPBMC | 2/16* |
| 2-OH-βCD administered intravaginally prior to infected HuPBMC challenge | 1/11* |

*P < 0.01 compared to PBS premixed with HuPBMC.

To examine the effect of a βCD on the vaginal epithelium, CF-1 mice were pretreated with progesterone and one week later were inoculated with 50 Tl of either phosphate buffered saline (PBS), 1% (w/v) nonoxynol-9, or 3% (w/v) 2-OH-βCD (20 mM) containing the membrane impermeant DNA binding fluorescent dye, ethidium bromide homodimer-1. The vaginas of the mice were viewed by fluorescent microscopy. 1% nonoxynol-9 caused considerable epithelial damage. In contrast, the 2-OH-βCD-treated mice had only minimal membrane damage to the vaginal epithelial cells and appeared more similar to the vaginal epithelium of the PBS treated control mice.

These results demonstrate that a βCD can inhibit vaginal transmission of cell-associated HIV-1. In addition, the results demonstrate that the HuPBL-SCID mice are useful for examining the effectiveness of potential agents that can reduce the sexual transmission of sexually transmitted diseases.

EXAMPLE 4

β-Cyclodextrin Blocks Vaginal Transmission of HSV-2

This example demonstrates that a βCD can be used reduce the risk of transmission of HSV-2 into vaginal epithelial cells.

The ability of 2-OH-βCD to reduce the infectiousness of HIV-1 (Examples 2 and 3) led to an investigation as to the general applicability of βCDs to prevent the transmission of other sexually transmitted enveloped viruses. A well characterized HSV mouse vaginal challenge model was used to examine the effect of 2-OH-βCD on HSV-2 infection (Sherwood et al., supra, 1996). Adult female CD-1 mice (Charles River Breeding Laboratories; Wilmington Mass.) were injected subcutaneously with Depo-Provera® progestin (2 mg) to increase their sensitivity, then one week later the mice were inoculated intravaginally with $1\times10^4$ TCID$_{50}$ of cell-free HSV-2 strain G (10 ID$_{50}$) using a WIRETROL capillary micropipette (Drummond Scientific; Broomall Pa.). Infection was confirmed by lavage culture on newborn foreskin fibroblast cells (Biowhitaker). Prior to inoculation, HSV-2 was preincubated either with 3% 2-OH-βCD or with buffer.

Nine of nine mice inoculated with the HSV-2 that had been preincubated with buffer (positive control) became infected. In comparison, only 5 of 10 mice inoculated with the βCD treated HSV-2 became infected (p=0.022). These results demonstrate that βCD can reduce the infectiousness of HSV-2, and further demonstrate the general effectiveness of βCDs for reducing the risk of transmission of sexually transmitted pathogens, including sexually transmitted enveloped viruses.

EXAMPLE 5

Effectiveness of β-Cyclodetrin Against HSV-2

This example provides a method for determining the effectiveness of intravaginal administration of βCD to reduce the risk of transmission of HSV-2.

Adult female mice are treated with Depo-Provera® progestin as described in Example 4. One week later, the mice are treated with 10 Tl of Bartels Tissue Culture Refeeding Medium (Bartels; Issaquah Wash.) containing $1\times10^4$ TCID$_{50}$ of cell-free HSV-2 (see Example 4). In various groups of mice, the HSV-2 is treated with a βCD prior to inoculation, or the βCD is administered intravaginally either in a buffer solution or in a BufferGel gel composition prior to inoculation with buffer treated HSV-2. Appropriate controls include BufferGel gel, alone, or a different gel compound.

Animals are observed daily for signs of infection, including perivaginal erythema, vesicles, and hair loss. Asymptomatic infection is detected by vaginal lavage and culture: 20 Tl of Bartels Tissue Culture Refeeding Medium is pipetted in and out of the vagina 10 times, diluted to 0.1 ml, and placed on target human newborn foreskin diploid fibroblast cells (Biowhitaker). Cytopathic effect (CPE) is scored 48 hr later, and those with lavage cultures displaying CPE are considered infected.

EXAMPLE 6

Effectiveness of β-Cyclodextrin Against Chlamydia

This example provides a method for determining the effectiveness of intravaginal administration of βCD to reduce the risk of transmission of a bacterial sexually transmitted pathogen, *Chlamydia trachomatis*.

A *C. trachomatis* mouse vaginal transmission model is used. Briefly, 6 to 8 week old specific pathogen-free outbred CF-1 female mice are pretreated subcutaneously with Depo-Provera® as described in Example 4. One week later, the mice are inoculated with *C. trachomatis* serovar D ("Ct-D"; ATCC Accession No. VR-885), which are propagated in McCoy cells (ATCC). On the day of inoculation, 50 Tl βCD (0, 1, 3 or 10% in saline) is delivered intravaginally using a 50 Tl WIRETROL pipette, and stirred to mimic the stirring effect of human coitus. Thirty min after delivery of the βCD, $1\times10^5$ inclusion forming units (ifu) of Ct-D (10 ID$_{50}$) suspended in 10 Tl of sucrose-phosphate transport medium is deposited in the vagina using a 10 Tl WIRETROL pipette.

Transmission is detected by determining the presence of Ct-D in the lower genital tract by culture. Vaginal swabs (Type 1 DACROSWAB swabs; Spectrum Laboratories; Dallas Tex.) are taken from each mouse on days 4 and 8 post-inoculation. Swabs are placed in transport medium and frozen in test tubes at −80° C. Specimens are plated in duplicate on semi-confluent McCoy cells, and the duplicate plate frozen following 72 hr of incubation. After iodine staining and evaluation of the primary plate, the duplicate plate is thawed and those specimens that are negative on the primary culture are transferred onto fresh McCoy cell monolayers for secondary (amplified) culture. Any positive culture result, either primary or secondary cultures on one or both days, is considered a productive infection.

Although the invention has been described with reference to the above examples, it will be understood that modifications and variations are encompassed within the spirit and scope of the invention. Accordingly, the invention is limited only by the following claims.

What is claimed is:

1. A method for treating a subject infected with a pathogen comprising, administering a therapeutically effective amount of a composition comprising an active agent to the subject, wherein the active agent is a β-cyclodextrin, thereby treating the subject.

2. The method of claim 1, wherein the pathogen is a virus.

3. The method of claim 2, wherein the virus is an enveloped virus.

4. The method of claim 3, wherein the enveloped virus is selected from the group consisting of a T lymphotrophic virus, human immunodeficiency virus (HIV), herpes simplex virus (HSV), and influenza virus.

5. The method of claim 2, wherein the virus is a human immunodeficiency virus.

6. The method of claim 2, wherein the virus is a herpes simplex virus.

7. The method of claim 2, wherein the virus is influenza virus.

8. The method of claim 1, wherein the pathogen is a microbial pathogen.

9. The method of claim 8, wherein the microbial pathogen is a bacterium, a yeast, or a protozoan.

10. The method of claim 9, wherein the microbial pathogen is a *Chlamydia* spp., a *Trichomona* spp., or a *Candida* spp.

11. The method of claim 1, wherein the β-cyclodextrin is formulated in a solution, a gel, a foam, an ointment, a cream, a paste, or a spray.

12. The method of claim 1, wherein the β-cyclodextrin is formulated in a suppository, a film, a contraceptive, an agent for treating a sexually transmitted disease, a lubricant, or a combination thereof.

13. The method of claim 1, wherein the composition further comprises an agent selected from the group consisting of a contraceptive, an agent for treating a sexually transmitted disease, a lubricant, and a combination thereof.

14. The method of claim 12, wherein the contraceptive is selected from the group consisting of a diaphragm, a vaginal disk, a vaginal film, a sponge, a spermicide, and a condom.

15. The method of claim 13, wherein the contraceptive is selected from the group consisting of a diaphragm, a vaginal disk, a vaginal film, a sponge, a spermicide, and a condom.

16. The method of claim 1, wherein the subject is a vertebrate.

17. The method of claim 1, wherein the subject is a human.

18. A method for treating a subject infected with a pathogen comprising, administering a therapeutically effective amount of a composition consisting of a β-cyclodextrin to the subject, thereby treating the subject.

19. A method for treating a subject infected with a pathogen comprising, administering a therapeutically effective amount of a composition consisting of a β-cyclodextrin and at least one additional active agent other than β-cyclodextrin to the subject, thereby treating the subject.

* * * * *